United States Patent
Larsen

(10) Patent No.: US 10,184,129 B2
(45) Date of Patent: Jan. 22, 2019

(54) METHOD AND COMPOSITIONS TO PROMOTE PLANT GROWTH IN METAL CONTAMINATED ENVIRONMENTS

(75) Inventor: Paul Brian Larsen, Riverside, CA (US)

(73) Assignee: The Regents of the University of California, Oakland, CA (US)

( * ) Notice: Subject to any disclaimer, the term of this patent is extended or adjusted under 35 U.S.C. 154(b) by 274 days.

(21) Appl. No.: 14/116,121

(22) PCT Filed: May 9, 2012

(86) PCT No.: PCT/US2012/037165
§ 371 (c)(1),
(2), (4) Date: Feb. 3, 2014

(87) PCT Pub. No.: WO2012/154884
PCT Pub. Date: Nov. 15, 2012

(65) Prior Publication Data
US 2014/0213455 A1    Jul. 31, 2014

Related U.S. Application Data

(60) Provisional application No. 61/484,007, filed on May 9, 2011.

(51) Int. Cl.
*C12N 15/82* (2006.01)
*C07K 14/415* (2006.01)
*A01N 33/04* (2006.01)
*C02F 3/32* (2006.01)
*C02F 101/20* (2006.01)

(52) U.S. Cl.
CPC ......... *C12N 15/8259* (2013.01); *A01N 33/04* (2013.01); *C02F 3/327* (2013.01); *C07K 14/415* (2013.01); *C12N 15/8243* (2013.01); *C12N 15/8271* (2013.01); *C02F 2101/20* (2013.01); *Y02W 10/18* (2015.05)

(58) Field of Classification Search
None
See application file for complete search history.

(56) References Cited

U.S. PATENT DOCUMENTS

2006/0225154 A1   10/2006   Kasukabe et al.
2008/0010702 A1   1/2008    Kasukabe et al.

OTHER PUBLICATIONS

Larsen et al. Plant Physiol. vol. 110, pp. 743-751. publication year: 1996.*
Gill et al. Polyamines and abiotic stress tolerance in plants. Plant Signaling and Behavior. 5:1, 26-33; Jan. 2010.*
Groppa et al. Polyamines and abiotic stress: recent advances. Amino Acids. (2008) 34:35-45.*
Larsen et al. *Arabidopsis* mutants with increased sensitivity to aluminum. Plant Physiol. Mar. 1996;110(3):743-51.*
Wen et al. Aluminum tolerance in a spermidine synthase-overexpressing transgenic European pear is correlated with the enhanced level of spermidine via alleviating oxidative status. Environmental and Experimental Botany. 66 (2009) 471-478.*
Mohapatra et al. The response of high and low polyamine-producing cell lines to aluminum and calcium stress. Plant Physiology and Biochemistry. 48 (2010) 612-620.*
Hauser et al. Trichome distribution in *Arabidopsis thaliana* and its close relative *Arabidopsis lyrata*: molecular analysis of the candidate gene GLABROUS1. Mol Biol Evol. Sep. 2001;18(9):1754-63. (Year: 2001).*
Bushell et al. The basis of natural and artificial postzygotic hybridization barriers in *Arabidopsis* species. Plant Cell. Jun. 2003;15(6): 1430-42. (Year: 2003).*
Baharlou, Simin, International Preliminary Report on Patentability, PCT/US2012/037165, The International Bureau of WIPO, dated Nov. 12, 2013.
Kim, Jae Hyun, International Search Report and Written Opinion, PCT/US2012/037165, Korean Intellectual Property Office, dated Jan. 2, 2013.
Wang et al., "Exogenous polyamines enhance copper tolerance of Nymphoides peltatum," J. Plant Physiol., vol. 164, pp. 1062-1070, 2007.
Wen et al., "Aluminum tolerance in a spermidine synthase-overexpressing transgenic European pear is correlated with the enhanced level of spermidine via alleviating oxdative status," Environ. and Exper. Botany, vol. 66, pp. 471-478, 2009.

* cited by examiner

*Primary Examiner* — Cynthia E Collins
(74) *Attorney, Agent, or Firm* — Gavrilovich, Dodd & Lindsey LLP

(57) ABSTRACT

The disclosure provides polynucleotides, polypeptides, transgenic plants, cells and vectors useful for crop plants to augment the basal level of aluminum and heavy metal tolerance.

6 Claims, 6 Drawing Sheets
Specification includes a Sequence Listing.

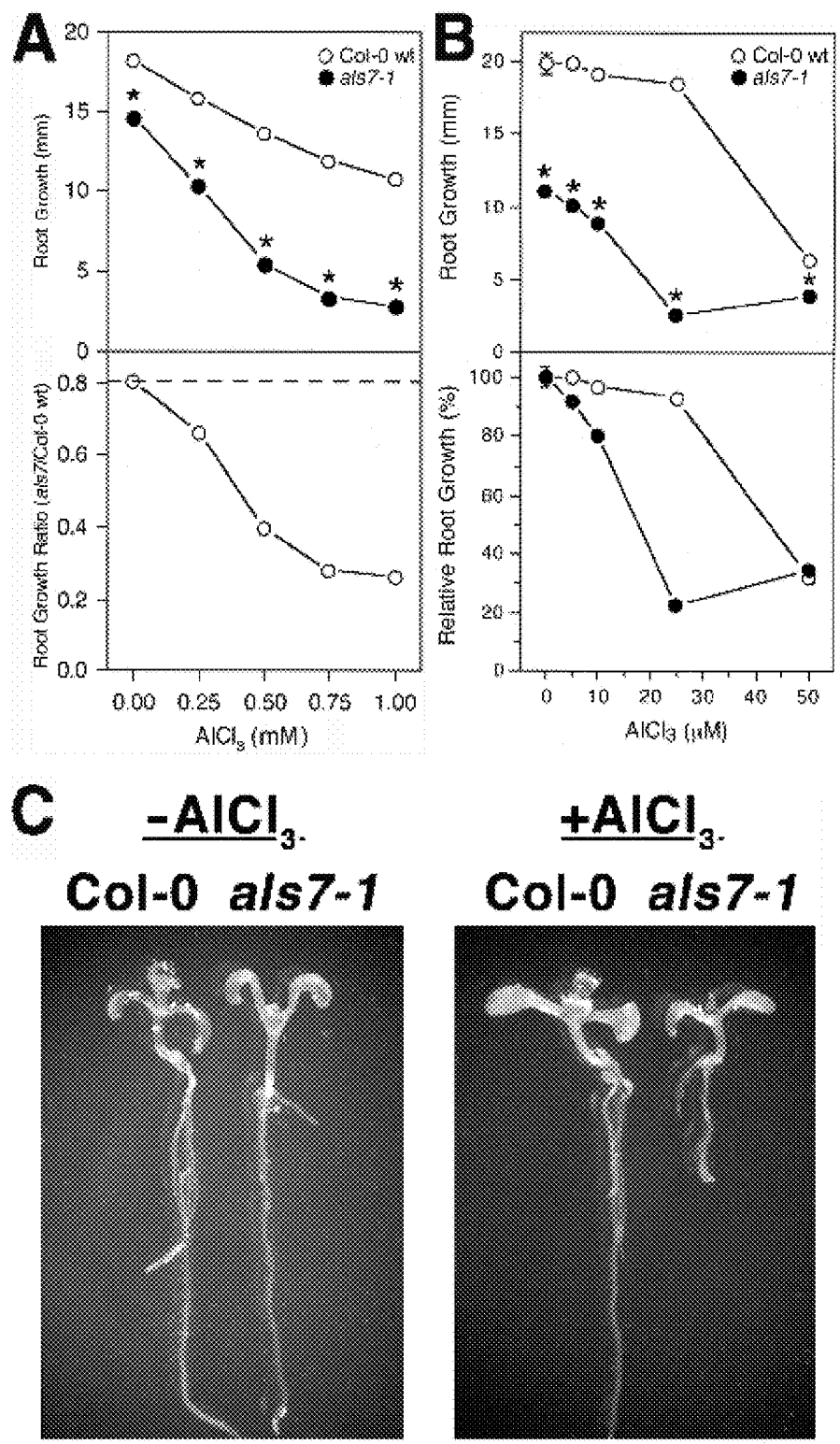
FIGURE 1A-C

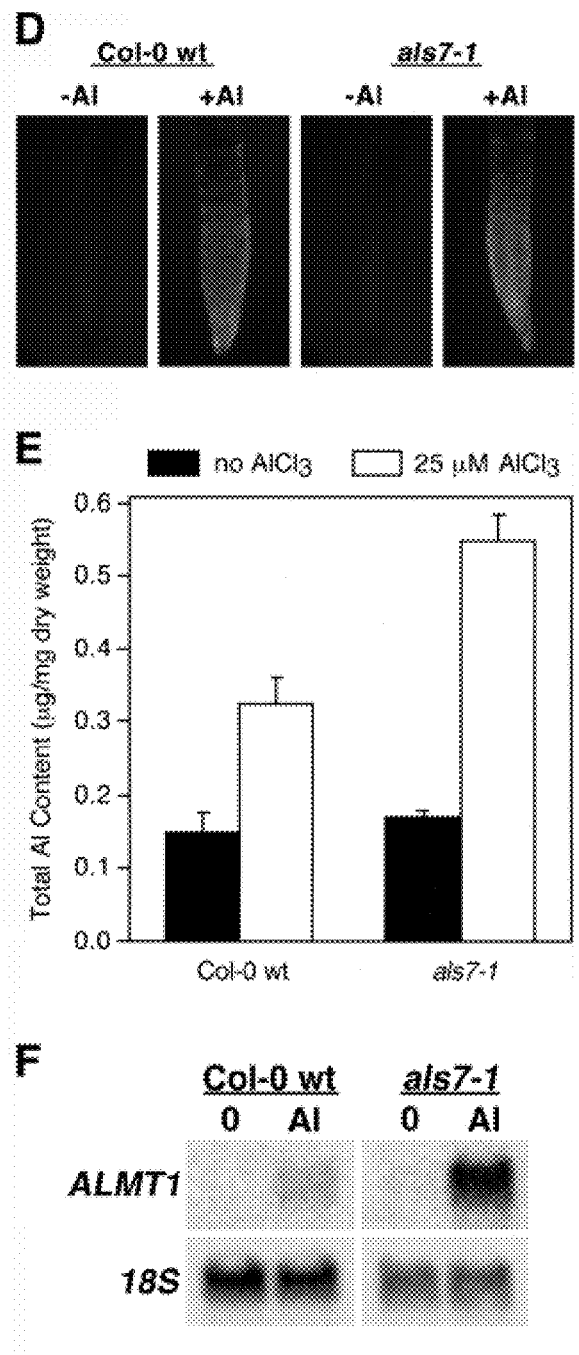
FIGURE 1D-F

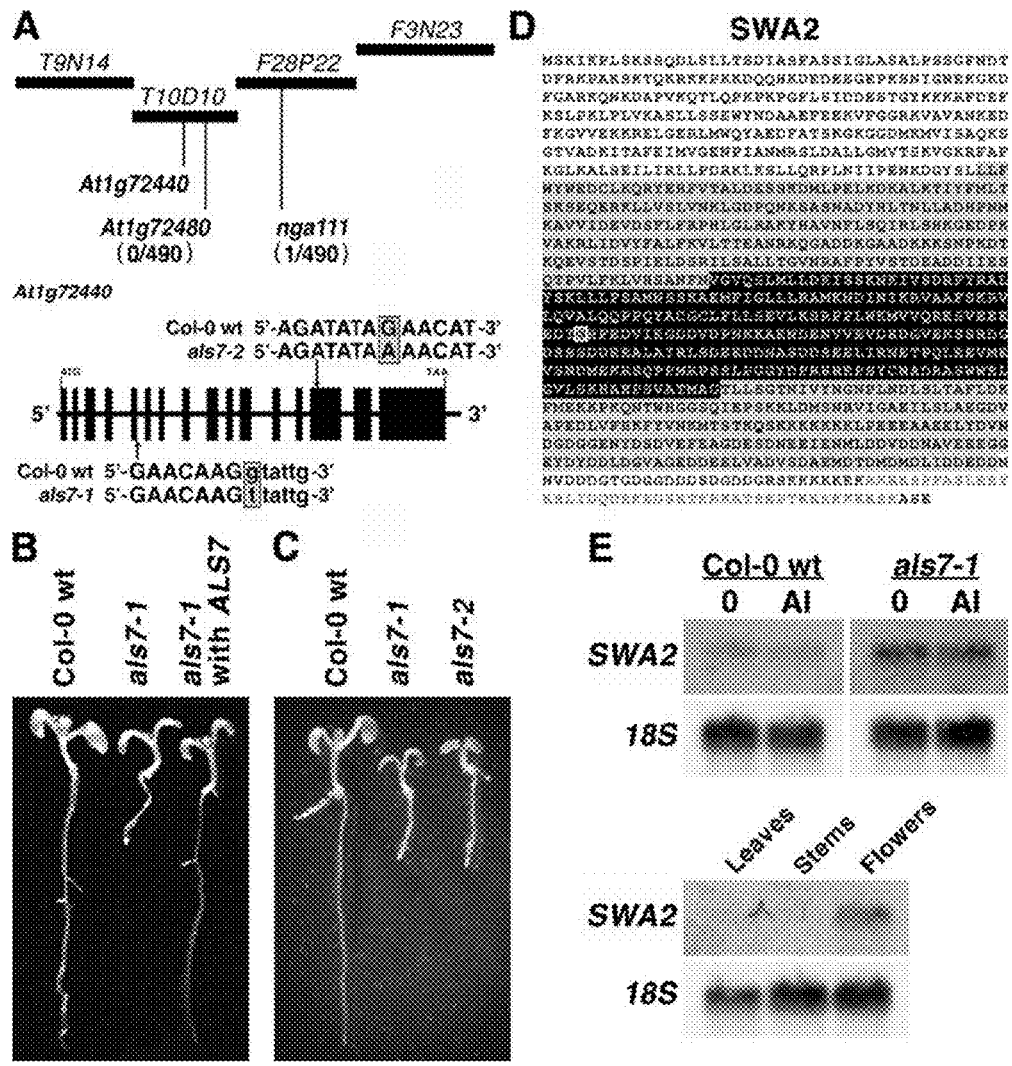
FIGURE 2A-E

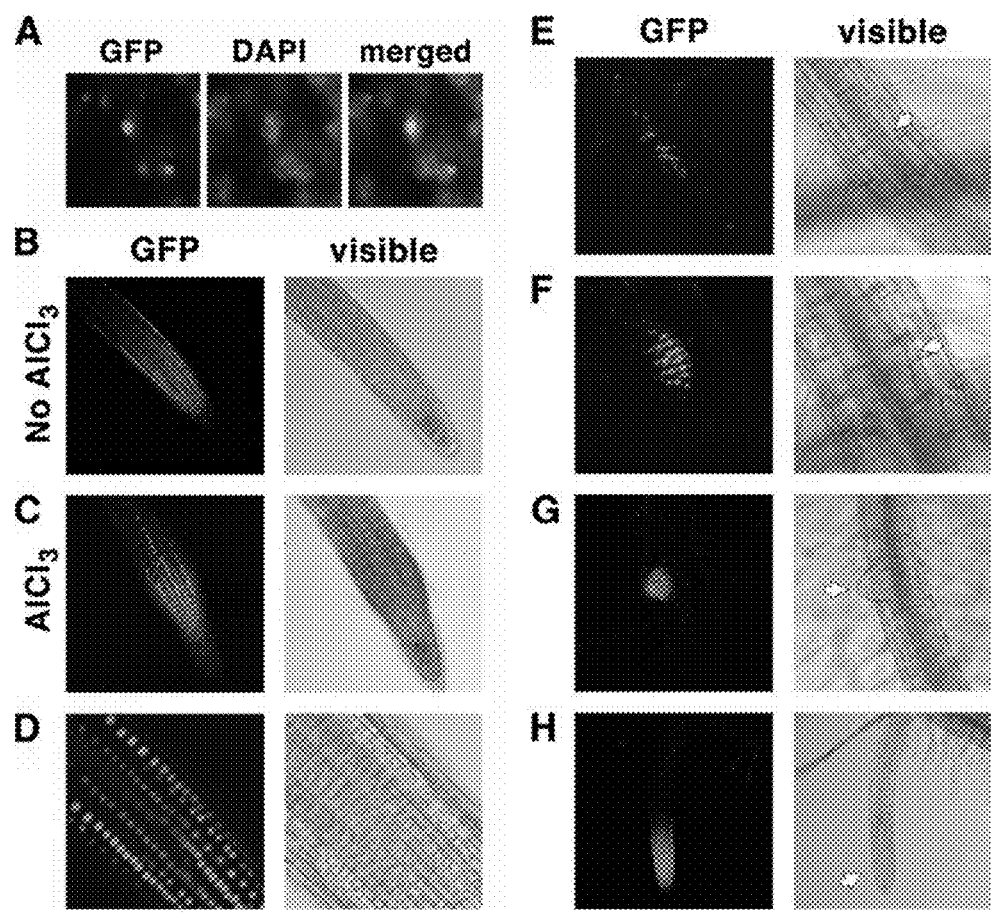
FIGURE 3A-H

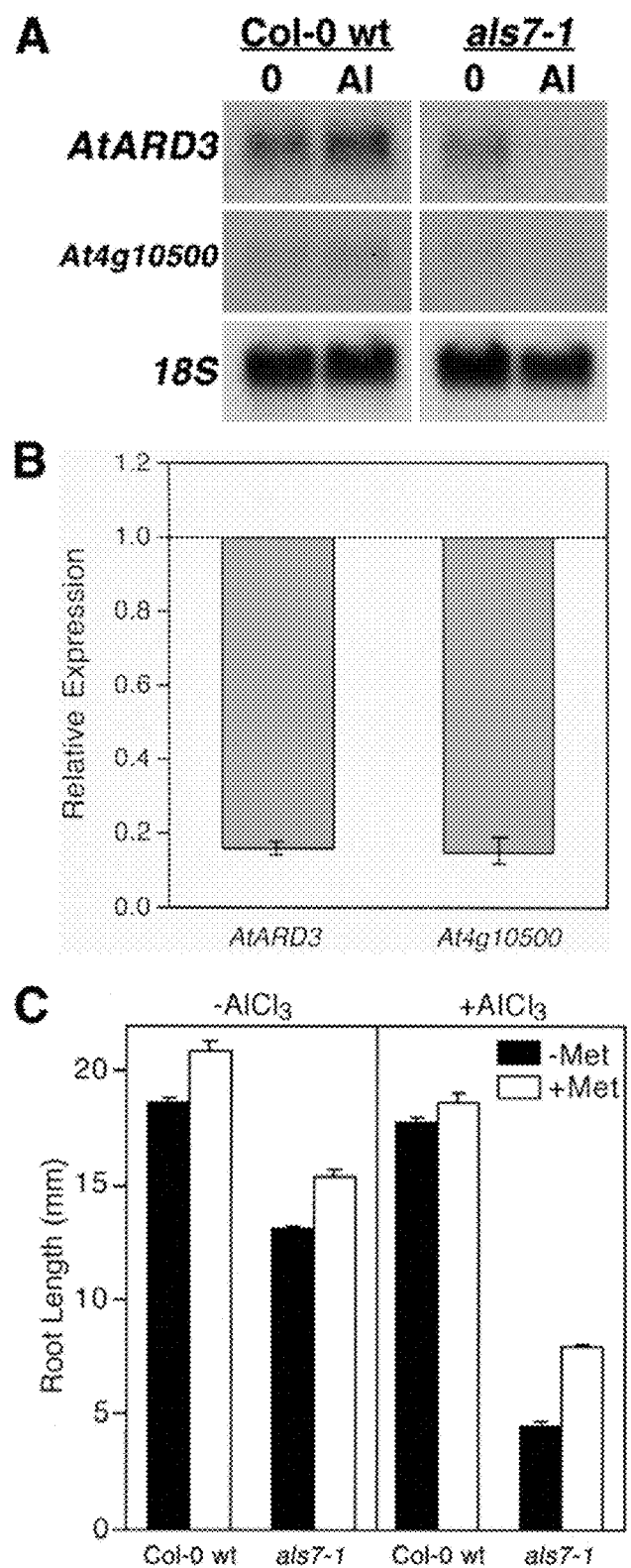
FIGURE 4A-C

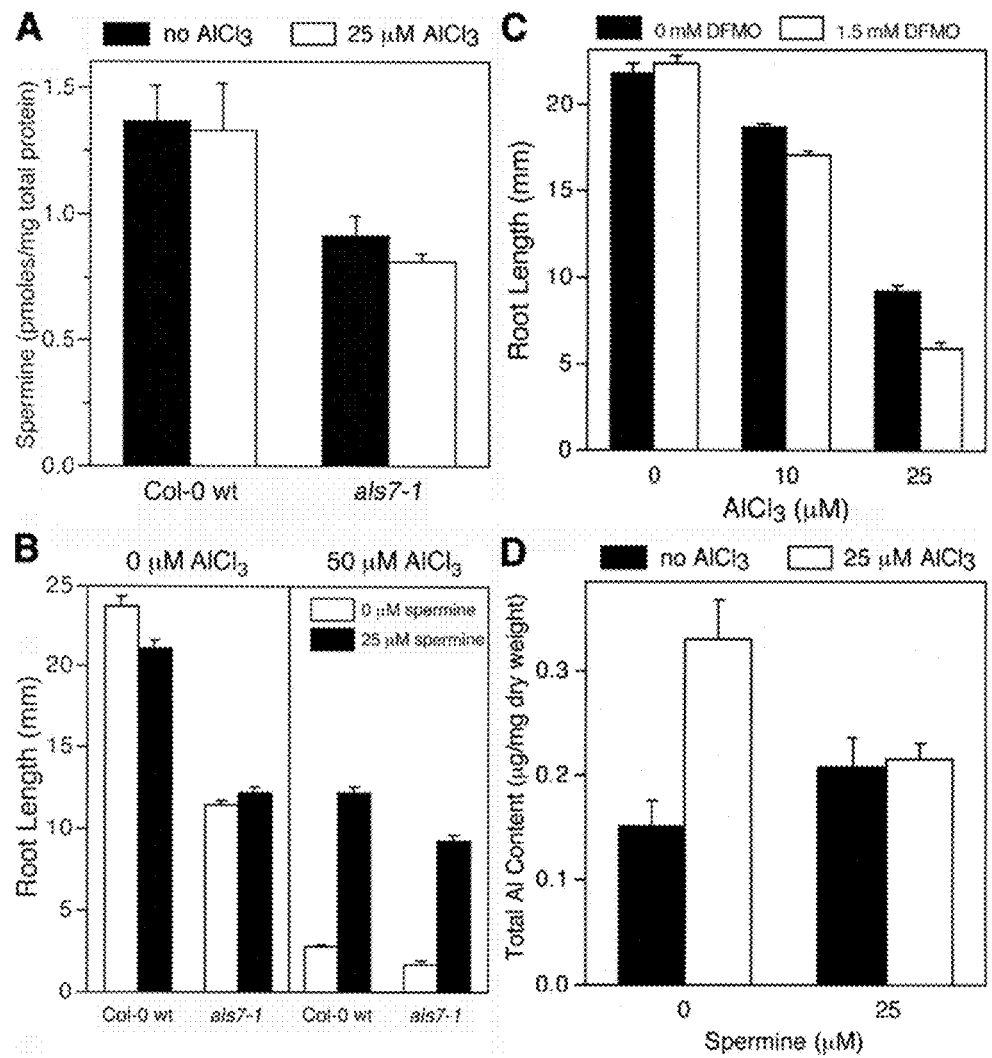
FIGURE 5A-D

SEQUENCE LISTING

```
<160> NUMBER OF SEQ ID NOS: 15

<210> SEQ ID NO 1
<211> LENGTH: 21
<212> TYPE: DNA
<213> ORGANISM: Artificial Sequence
<220> FEATURE:
<223> OTHER INFORMATION: Forward Primer for marker At1g72480

<400> SEQUENCE: 1
atgcagaagc gaatagcctt g                                                   21

<210> SEQ ID NO 2
<211> LENGTH: 21
<212> TYPE: DNA
<213> ORGANISM: Artificial Sequence
<220> FEATURE:
<223> OTHER INFORMATION: Reverse primer for marker At1g72480

<400> SEQUENCE: 2
caaaatccag ataagcacct c                                                   21

<210> SEQ ID NO 3
<211> LENGTH: 23
<212> TYPE: DNA
<213> ORGANISM: Artificial Sequence
<220> FEATURE:
<223> OTHER INFORMATION: Forward primer for AtARD3

<400> SEQUENCE: 3
aagatacaaa ttccttagga tcc                                                 23

<210> SEQ ID NO 4
<211> LENGTH: 23
<212> TYPE: DNA
<213> ORGANISM: Artificial Sequence
<220> FEATURE:
<223> OTHER INFORMATION: Reverse primer for AtARD3

<400> SEQUENCE: 4
acacaaaaga agaataacca tgg                                                 23

<210> SEQ ID NO 5
<211> LENGTH: 22
<212> TYPE: DNA
<213> ORGANISM: Artificial Sequence
<220> FEATURE:
<223> OTHER INFORMATION: Forward primer for At4g10500
```

<400> SEQUENCE: 5 ttccgactttctatttccctttc          22

<210> SEQ ID NO 6
<211> LENGTH: 23
<212> TYPE: DNA
<213> ORGANISM: Artificial Sequence
<220> FEATURE:
<223> OTHER INFORMATION: Reverse primer for At4g10500

<400> SEQUENCE: 6
atagcttaaa gagccaattc aag          23

<210> SEQ ID NO 7
<211> LENGTH: 1043
<212> TYPE: PRT
<213> ORGANISM: Arabidopsis thaliana

<400> SEQUENCE: 7

Met Ser Lys Ile Lys Pro Leu Ser Lys Ser Ser Gln Asp Leu Ser Leu
1               5                   10                  15

Leu Thr Ser Asp Ile Ala Ser Phe Ala Ser Ser Ile Gly Leu Ala Ser
            20                  25                  30

Ala Leu Pro Ser Ser Gly Phe Asn Asp Thr Asp Phe Arg Lys Pro Ala
        35                  40                  45

Lys Ser Lys Thr Gln Lys Arg Lys Lys Pro Lys Lys Asp Gln Gln His
    50                  55                  60

Lys Asp Glu Asp Glu Glu Gly Glu Pro Lys Ser Asn Ile Gly Asn Glu
65                  70                  75                  80

Lys Gly Lys Asp Phe Gly Ala Arg Lys Gln Asn Lys Asp Ala Pro Val
                85                  90                  95

Lys Gln Thr Leu Gln Pro Lys Pro Lys Pro Gly Phe Leu Ser Ile Asp
            100                 105                 110

Asp Glu Ser Thr Gly Tyr Lys Lys Lys Arg Phe Asp Glu Phe Lys Ser
        115                 120                 125

Leu Pro Lys Leu Pro Leu Val Lys Ala Ser Leu Leu Ser Ser Glu Trp
    130                 135                 140

Tyr Asn Asp Ala Ala Glu Phe Glu Glu Lys Val Phe Gly Gly Arg Lys
145                 150                 155                 160

Val Ala Val Ala Asn Lys Glu Asp Phe Lys Gly Val Val Glu Lys Lys
                165                 170                 175

Arg Glu Leu Gly Glu Arg Leu Met Trp Gln Tyr Ala Glu Asp Phe Ala
            180                 185                 190

Thr Ser Lys Gly Lys Gly Gly Asp Met Lys Met Val Ile Ser Ala Gln
        195                 200                 205

Lys Ser Gly Thr Val Ala Asp Lys Ile Thr Ala Phe Glu Ile Met Val
    210                 215                 220

Gly Glu Asn Pro Ile Ala Asn Met Arg Ser Leu Asp Ala Leu Leu Gly
225                 230                 235                 240

Met Val Thr Ser Lys Val Gly Lys Arg Phe Ala Phe Lys Gly Leu Lys
                245                 250                 255

Ala Leu Ser Glu Ile Leu Ile Arg Leu Pro Asp Arg Lys Leu Lys
            260                 265                 270

Ser Leu Leu Gln Arg Pro Leu Asn Ile Ile Pro Glu Asn Lys Asp Gly
    275                 280                 285

Tyr Ser Leu Leu Leu Phe Trp Tyr Trp Glu Asp Cys Leu Lys Gln Arg

```
                      290                 295                 300
Tyr Glu Arg Phe Val Thr Ala Leu Asp Glu Ser Ser Lys Asp Met Leu
305                 310                 315                 320

Pro Glu Leu Lys Asp Lys Ala Leu Lys Thr Ile Tyr Phe Met Leu Thr
                    325                 330                 335

Ser Lys Ser Glu Gln Glu Arg Lys Leu Leu Val Ser Leu Val Asn Lys
                340                 345                 350

Leu Gly Asp Pro Gln Asn Lys Ser Ala Ser Asn Ala Asp Tyr His Leu
                    355                 360                 365

Thr Asn Leu Leu Ala Asp His Pro Asn Met Lys Ala Val Ile Asp
    370                 375                 380

Glu Val Asp Ser Phe Leu Phe Arg Pro His Leu Gly Leu Arg Ala Lys
385                 390                 395                 400

Tyr His Ala Val Asn Phe Leu Ser Gln Ile Arg Leu Ser His Lys Gly
                    405                 410                 415

Glu Asp Pro Lys Val Ala Lys Arg Leu Ile Asp Val Tyr Phe Ala Leu
                420                 425                 430

Phe Lys Val Leu Thr Thr Glu Ala Asn Arg Lys Gln Gly Ala Asp Asp
    435                 440                 445

Lys Gly Ala Ala Asp Lys Lys Lys Ser Asn Pro Lys Asp Thr Lys Gln
    450                 455                 460

Glu Val Ser Thr Asp Ser Pro Ile Glu Leu Asp Ser Arg Ile Leu Ser
465                 470                 475                 480

Ala Leu Leu Thr Gly Val Asn Arg Ala Phe Pro Tyr Val Ser Thr Asp
                    485                 490                 495

Glu Ala Asp Asp Ile Ile Glu Ser Gln Thr Pro Val Leu Phe Lys Leu
                500                 505                 510

Val His Ser Ala Asn Phe Asn Val Gly Val Gln Ser Leu Met Leu Leu
                    515                 520                 525

Asp Lys Ile Ser Ser Lys Asn Lys Ile Val Ser Asp Arg Phe Tyr Arg
    530                 535                 540

Ala Leu Tyr Ser Lys Leu Leu Pro Ser Ala Met Asn Ser Ser Lys
545                 550                 555                 560

Ala Glu Met Phe Ile Gly Leu Leu Leu Arg Ala Met Lys Asn Asp Ile
                565                 570                 575

Asn Ile Lys Arg Val Ala Ala Phe Ser Lys Arg Val Leu Gln Val Ala
                580                 585                 590

Leu Gln Gln Pro Pro Gln Tyr Ala Cys Gly Cys Leu Phe Leu Leu Ser
                    595                 600                 605

Glu Val Leu Lys Ser Arg Pro Pro Leu Trp Lys Met Val Val Gln Arg
                610                 615                 620

Glu Ser Val Glu Glu Glu Asp Leu Glu His Phe Glu Asp Val Ile
625                 630                 635                 640

Glu Gly Asp Asp Val Asp Pro Asn Lys Lys Ala Glu Asn Asp Asn
                    645                 650                 655

Val Val Glu Val Asp His Asp Gly Val Glu Lys Ser Ser Arg Asp Gly
                660                 665                 670

Asp Ser Ser Ser Asp Asp Glu Glu Ala Leu Ala Ile Arg Leu Ser Asp
                    675                 680                 685

Glu Glu Asp Asp Asn Ala Ser Asp Asp Ser Glu Glu Leu Ile Arg Asn
                690                 695                 700

Glu Thr Pro Gln Leu Glu Glu Val Met Glu Val Ser Asn Asp Met Glu
705                 710                 715                 720
```

```
Lys Arg Ser Gln Pro Pro Met Arg Pro Ser Ser Leu Pro Gly Gly Tyr
                725                 730                 735

Asp Pro Arg His Arg Glu Pro Ser Tyr Cys Asn Ala Asp Arg Ala Ser
            740                 745                 750

Trp Trp Glu Leu Gly Val Leu Ser Lys His Ala His Pro Ser Val Ala
        755                 760                 765

Thr Met Ala Gly Thr Leu Leu Ser Gly Thr Asn Ile Val Tyr Asn Gly
    770                 775                 780

Asn Pro Leu Asn Asp Leu Ser Leu Thr Ala Phe Leu Asp Lys Phe Met
785                 790                 795                 800

Glu Lys Lys Pro Lys Gln Asn Thr Trp His Gly Gly Ser Gln Ile Glu
                805                 810                 815

Pro Ser Lys Lys Leu Asp Met Ser Asn Arg Val Ile Gly Ala Glu Ile
            820                 825                 830

Leu Ser Leu Ala Glu Gly Asp Val Ala Pro Glu Asp Leu Val Phe His
        835                 840                 845

Lys Phe Tyr Val Asn Lys Met Thr Ser Thr Lys Gln Ser Lys Lys Lys
    850                 855                 860

Lys Lys Lys Lys Leu Pro Glu Glu Ala Ala Glu Glu Leu Tyr Asp
865                 870                 875                 880

Val Asn Asp Gly Asp Gly Gly Glu Asn Tyr Asp Ser Asp Val Glu Phe
                885                 890                 895

Glu Ala Gly Asp Glu Ser Asp Asn Glu Ile Glu Asn Met Leu Asp
            900                 905                 910

Asp Val Asp Asp Asn Ala Val Glu Glu Gly Gly Glu Tyr Asp Tyr
        915                 920                 925

Asp Asp Leu Asp Gly Val Ala Gly Glu Asp Glu Glu Leu Val Ala
    930                 935                 940

Asp Val Ser Asp Ala Glu Met Asp Thr Asp Met Asp Met Asp Leu Ile
945                 950                 955                 960

Asp Asp Glu Asp Asp Asn Asn Val Asp Asp Gly Thr Gly Asp Gly
                965                 970                 975

Gly Asp Asp Asp Ser Asp Gly Asp Gly Arg Ser Lys Lys Lys
            980                 985                 990

Lys Glu Lys Arg Lys Arg Lys Ser Pro Phe Ala Ser Leu Glu Glu Tyr
        995                 1000                1005

Lys His Leu Ile Asp Gln Asp Glu Lys Glu Asp Ser Lys Thr Lys
    1010                1015                1020

Arg Lys Ala Thr Ser Glu Pro Thr Lys Lys Lys Lys Lys Lys
    1025                1030                1035

Ser Lys Ala Ser Glu
    1040

<210> SEQ ID NO 8
<211> LENGTH: 1080
<212> TYPE: DNA
<213> ORGANISM: Arabidopsis thaliana
<220> FEATURE:
<221> NAME/KEY: CDS
<222> LOCATION: (1)..(1080)

<400> SEQUENCE: 8 atg gag gga gac gtc gga ata ggt ttg gta tgc cag aat act atg gat      48
Met Glu Gly Asp Val Gly Ile Gly Leu Val Cys Gln Asn Thr Met Asp
1               5                   10                  15
```

-continued

| | | |
|---|---|---|
| ggg aag gcg agt aat gga aat ggt tta gag aag act gta cct tct tgt<br>Gly Lys Ala Ser Asn Gly Asn Gly Leu Glu Lys Thr Val Pro Ser Cys<br>20                            25                        30 | 96 |
| tgc ctt aag gct atg gca tgt gta cct gag gat gat gct aag tgt cac<br>Cys Leu Lys Ala Met Ala Cys Val Pro Glu Asp Asp Ala Lys Cys His<br>35                        40                        45 | 144 |
| tcc act gtt gtt tct ggg tgg ttt tcg gaa cct cac cct cgc tct ggg<br>Ser Thr Val Val Ser Gly Trp Phe Ser Glu Pro His Pro Arg Ser Gly<br>50                        55                        60 | 192 |
| aaa aaa ggc ggc aaa gca gtc tat ttc aac aac cct atg tgg cca gga<br>Lys Lys Gly Gly Lys Ala Val Tyr Phe Asn Asn Pro Met Trp Pro Gly<br>65                        70                        75                        80 | 240 |
| gaa gca cac tca ctg aaa gtt gag aaa gtt ctg ttc aaa gac aag tcg<br>Glu Ala His Ser Leu Lys Val Glu Lys Val Leu Phe Lys Asp Lys Ser<br>                        85                        90                        95 | 288 |
| gat ttt cag gaa gtc cta gtg ttc gag tca gcc acg tac gga aag gtg<br>Asp Phe Gln Glu Val Leu Val Phe Glu Ser Ala Thr Tyr Gly Lys Val<br>                        100                    105                 110 | 336 |
| ctt gtt cta gat ggt atc gta cag ctg acc gaa aaa gat gaa tgt gca<br>Leu Val Leu Asp Gly Ile Val Gln Leu Thr Glu Lys Asp Glu Cys Ala<br>                        115                    120                 125 | 384 |
| tat cag gag atg ata gcc cat ctg cct tta tgc tct ata tct tcc cct<br>Tyr Gln Glu Met Ile Ala His Leu Pro Leu Cys Ser Ile Ser Ser Pro<br>130                        135                    140 | 432 |
| aaa aat gtt ctt gtt gtt ggt gga ggt gat ggt ggt gtt ctt cga gag<br>Lys Asn Val Leu Val Val Gly Gly Gly Asp Gly Gly Val Leu Arg Glu<br>145                        150                    155                 160 | 480 |
| att tct cgc cat agt tct gtt gag gtt att gat atc tgt gag ata gac<br>Ile Ser Arg His Ser Ser Val Glu Val Ile Asp Ile Cys Glu Ile Asp<br>                        165                    170                 175 | 528 |
| aag atg gtt ata gat gtg tct aag aag ttc ttc ccc gag tta gcg gtt<br>Lys Met Val Ile Asp Val Ser Lys Lys Phe Phe Pro Glu Leu Ala Val<br>                        180                    185                 190 | 576 |
| ggg ttt gac gat cct cgt gtt caa ctt cac att ggt gat gct gct gag<br>Gly Phe Asp Asp Pro Arg Val Gln Leu His Ile Gly Asp Ala Ala Glu<br>                        195                    200                 205 | 624 |
| ttc ctc cgt aaa tcc cct gaa ggg aag tat gat gcc atc att gtt gat<br>Phe Leu Arg Lys Ser Pro Glu Gly Lys Tyr Asp Ala Ile Ile Val Asp<br>210                        215                    220 | 672 |
| tct tca gat ccc gta ggt cct gct ctt gcg ctt gtt gag aag cct ttc<br>Ser Ser Asp Pro Val Gly Pro Ala Leu Ala Leu Val Glu Lys Pro Phe<br>225                        230                    235                 240 | 720 |
| ttc gag aca ctg gct aga gcg ttg aag cct ggg gga gtt ctt tgt aac<br>Phe Glu Thr Leu Ala Arg Ala Leu Lys Pro Gly Gly Val Leu Cys Asn<br>                        245                    250                 255 | 768 |
| atg gca gaa agt atg tgg ctc cat act cat ctt att gaa gat atg atc<br>Met Ala Glu Ser Met Trp Leu His Thr His Leu Ile Glu Asp Met Ile<br>                        260                    265                 270 | 816 |
| tcc att tgc cgt caa aca ttc aaa agt gtt cac tat gcg tgg agc agc<br>Ser Ile Cys Arg Gln Thr Phe Lys Ser Val His Tyr Ala Trp Ser Ser<br>275                        280                    285 | 864 |
| gtc ccc aca tat cca agc ggc gtg att ggt ttc gtc ttg tgc tct act<br>Val Pro Thr Tyr Pro Ser Gly Val Ile Gly Phe Val Leu Cys Ser Thr<br>290                        295                    300 | 912 |
| gaa gga cca gct gtt gac ttc aag aac cca atc aac cct att gag aaa<br>Glu Gly Pro Ala Val Asp Phe Lys Asn Pro Ile Asn Pro Ile Glu Lys<br>305                        310                    315                 320 | 960 |
| cta gac ggt gcg atg acc cat aaa aga gaa ttg aag ttc tat aac tct<br>Leu Asp Gly Ala Met Thr His Lys Arg Glu Leu Lys Phe Tyr Asn Ser<br>                        325                    330                 335 | 1008 |

```
gat atg cac aga gcc gca ttt gct ttg ccc aca ttc ctg cgg aga gaa      1056
Asp Met His Arg Ala Ala Phe Ala Leu Pro Thr Phe Leu Arg Arg Glu
        340                 345                 350 gta gct tca ctt ctg gct tct tga                                      1080
Val Ala Ser Leu Leu Ala Ser
        355
```

<210> SEQ ID NO 9
<211> LENGTH: 359
<212> TYPE: PRT
<213> ORGANISM: Arabidopsis thaliana

<400> SEQUENCE: 9

```
Met Glu Gly Asp Val Gly Ile Gly Leu Val Cys Gln Asn Thr Met Asp
1               5                   10                  15

Gly Lys Ala Ser Asn Gly Asn Gly Leu Glu Lys Thr Val Pro Ser Cys
            20                  25                  30

Cys Leu Lys Ala Met Ala Cys Val Pro Glu Asp Asp Ala Lys Cys His
        35                  40                  45

Ser Thr Val Val Ser Gly Trp Phe Ser Glu Pro His Pro Arg Ser Gly
    50                  55                  60

Lys Lys Gly Gly Lys Ala Val Tyr Phe Asn Asn Pro Met Trp Pro Gly
65                  70                  75                  80

Glu Ala His Ser Leu Lys Val Glu Lys Val Leu Phe Lys Asp Lys Ser
                85                  90                  95

Asp Phe Gln Glu Val Leu Val Phe Glu Ser Ala Thr Tyr Gly Lys Val
            100                 105                 110

Leu Val Leu Asp Gly Ile Val Gln Leu Thr Glu Lys Asp Glu Cys Ala
        115                 120                 125

Tyr Gln Glu Met Ile Ala His Leu Pro Leu Cys Ser Ile Ser Ser Pro
    130                 135                 140

Lys Asn Val Leu Val Val Gly Gly Asp Gly Gly Val Leu Arg Glu
145                 150                 155                 160

Ile Ser Arg His Ser Ser Val Glu Val Ile Asp Ile Cys Glu Ile Asp
                165                 170                 175

Lys Met Val Ile Asp Val Ser Lys Lys Phe Phe Pro Glu Leu Ala Val
            180                 185                 190

Gly Phe Asp Asp Pro Arg Val Gln Leu His Ile Gly Asp Ala Ala Glu
        195                 200                 205

Phe Leu Arg Lys Ser Pro Glu Gly Lys Tyr Asp Ala Ile Ile Val Asp
    210                 215                 220

Ser Ser Asp Pro Val Gly Pro Ala Leu Ala Leu Val Glu Lys Pro Phe
225                 230                 235                 240

Phe Glu Thr Leu Ala Arg Ala Leu Lys Pro Gly Gly Val Leu Cys Asn
                245                 250                 255

Met Ala Glu Ser Met Trp Leu His Thr His Leu Ile Glu Asp Met Ile
            260                 265                 270

Ser Ile Cys Arg Gln Thr Phe Lys Ser Val His Tyr Ala Trp Ser Ser
        275                 280                 285

Val Pro Thr Tyr Pro Ser Gly Val Ile Gly Phe Val Leu Cys Ser Thr
    290                 295                 300

Glu Gly Pro Ala Val Asp Phe Lys Asn Pro Ile Asn Pro Ile Glu Lys
305                 310                 315                 320

Leu Asp Gly Ala Met Thr His Lys Arg Glu Leu Lys Phe Tyr Asn Ser
                325                 330                 335
```

```
Asp Met His Arg Ala Ala Phe Ala Leu Pro Thr Phe Leu Arg Arg Glu
        340                 345                 350

Val Ala Ser Leu Leu Ala Ser
        355

<210> SEQ ID NO 10
<211> LENGTH: 1023
<212> TYPE: DNA
<213> ORGANISM: Arabidopsis thaliana
<220> FEATURE:
<221> NAME/KEY: CDS
<222> LOCATION: (1)..(1023)

<400> SEQUENCE: 10 atg tct tca aca caa gaa gcg tct gtt act gat ttg ccc gtg aag aga      48
Met Ser Ser Thr Gln Glu Ala Ser Val Thr Asp Leu Pro Val Lys Arg
  1               5                  10                  15 cct aga gaa gca gag gag gac aat aac ggc ggc gcc atg gaa aca gag      96
Pro Arg Glu Ala Glu Glu Asp Asn Asn Gly Gly Ala Met Glu Thr Glu
                 20                  25                  30 aac ggt gga gga gag ata aag gag cct tct tgt atg tcc tct att att     144
Asn Gly Gly Gly Glu Ile Lys Glu Pro Ser Cys Met Ser Ser Ile Ile
             35                  40                  45 cct gga tgg ttc tct gag att agt cct atg tgg cca gga gaa gca cat     192
Pro Gly Trp Phe Ser Glu Ile Ser Pro Met Trp Pro Gly Glu Ala His
         50                  55                  60 tct ctc aag gta gag aag att cta ttc caa ggg aaa tca gat tac cag     240
Ser Leu Lys Val Glu Lys Ile Leu Phe Gln Gly Lys Ser Asp Tyr Gln
 65                  70                  75                  80 gat gtt att gtt ttc cag tct gca aca tat gga aag gtt ttg gtt ttg     288
Asp Val Ile Val Phe Gln Ser Ala Thr Tyr Gly Lys Val Leu Val Leu
                 85                  90                  95 gat gga gtg att caa ctc act gag aga gat gaa tgt gcg tat caa gaa     336
Asp Gly Val Ile Gln Leu Thr Glu Arg Asp Glu Cys Ala Tyr Gln Glu
            100                 105                 110 atg atc act cat ctt cct ttg tgc tct atc tcc aac ccc aaa aag gta     384
Met Ile Thr His Leu Pro Leu Cys Ser Ile Ser Asn Pro Lys Lys Val
        115                 120                 125 ctg gtg att gga gga gga gat gga gga gtc ctg agg gaa gtg gca cgt     432
Leu Val Ile Gly Gly Gly Asp Gly Gly Val Leu Arg Glu Val Ala Arg
    130                 135                 140 cat agt tct gtt gag cag att gac att tgt gaa ata gat aaa atg gtg     480
His Ser Ser Val Glu Gln Ile Asp Ile Cys Glu Ile Asp Lys Met Val
145                 150                 155                 160 gtt gat gtg gct aag cag tat ttc cct aat gta gca gtt gga tac gag     528
Val Asp Val Ala Lys Gln Tyr Phe Pro Asn Val Ala Val Gly Tyr Glu
                165                 170                 175 gat cct cgt gtc aac ctc atc att ggc gat ggt gtt gct ttc ttg aag     576
Asp Pro Arg Val Asn Leu Ile Ile Gly Asp Gly Val Ala Phe Leu Lys
            180                 185                 190 aac gct gct gaa gga acc tat gat gca gtt att gtt gat tca tct gat     624
Asn Ala Ala Glu Gly Thr Tyr Asp Ala Val Ile Val Asp Ser Ser Asp
        195                 200                 205 cca atc ggt cca gca aaa gag cta ttt gag aaa cct ttc ttt gag tca     672
Pro Ile Gly Pro Ala Lys Glu Leu Phe Glu Lys Pro Phe Phe Glu Ser
    210                 215                 220 gtg aat aga gct ctt cgt cct ggt gga gtt gtg tgc aca caa gct gaa     720
Val Asn Arg Ala Leu Arg Pro Gly Gly Val Val Cys Thr Gln Ala Glu
225                 230                 235                 240 agc ttg tgg ctt cac atg gat atc att gaa gac att gtt tct aat tgc     768
```

| | | | | | | | | | | | |
|---|---|---|---|---|---|---|---|---|---|---|---|
| Ser | Leu | Trp | Leu | His | Met | Asp | Ile | Ile | Glu | Asp | Ile | Val | Ser | Asn | Cys |
| | | | 245 | | | | 250 | | | | 255 | | | | |

```
cgt gac atc ttt aaa gga tct gtt aac tac gct tgg acc agt gtt cca      816
Arg Asp Ile Phe Lys Gly Ser Val Asn Tyr Ala Trp Thr Ser Val Pro
        260                 265                 270 act tac ccg agt gga gtc att gga ttc atg ctt tgt tca tct gaa gga      864
Thr Tyr Pro Ser Gly Val Ile Gly Phe Met Leu Cys Ser Ser Glu Gly
            275                 280                 285 cca caa gtc gat ttc aag aag cca gtg agt cta atc gat act gat gaa      912
Pro Gln Val Asp Phe Lys Lys Pro Val Ser Leu Ile Asp Thr Asp Glu
    290                 295                 300 agc tct atc aaa tca cac tgt ccc ttg aag tat tac aac gct gag att      960
Ser Ser Ile Lys Ser His Cys Pro Leu Lys Tyr Tyr Asn Ala Glu Ile
305                 310                 315                 320 cac tca gct gct ttc tgc ttg ccc tct ttt gct aag aag gtg att gat     1008
His Ser Ala Ala Phe Cys Leu Pro Ser Phe Ala Lys Lys Val Ile Asp
                325                 330                 335 tcg aaa gcc aac tag                                                 1023
Ser Lys Ala Asn
            340
```

<210> SEQ ID NO 11
<211> LENGTH: 340
<212> TYPE: PRT
<213> ORGANISM: Arabidopsis thaliana

<400> SEQUENCE: 11

| Met | Ser | Ser | Thr | Gln | Glu | Ala | Ser | Val | Thr | Asp | Leu | Pro | Val | Lys | Arg |
|---|---|---|---|---|---|---|---|---|---|---|---|---|---|---|---|
| 1 | | | | 5 | | | | | 10 | | | | | 15 | |

| Pro | Arg | Glu | Ala | Glu | Glu | Asp | Asn | Asn | Gly | Gly | Ala | Met | Glu | Thr | Glu |
|---|---|---|---|---|---|---|---|---|---|---|---|---|---|---|---|
| | | | 20 | | | | | 25 | | | | | 30 | | |

| Asn | Gly | Gly | Gly | Glu | Ile | Lys | Glu | Pro | Ser | Cys | Met | Ser | Ser | Ile | Ile |
|---|---|---|---|---|---|---|---|---|---|---|---|---|---|---|---|
| | | 35 | | | | | 40 | | | | | 45 | | | |

| Pro | Gly | Trp | Phe | Ser | Glu | Ile | Ser | Pro | Met | Trp | Pro | Gly | Glu | Ala | His |
|---|---|---|---|---|---|---|---|---|---|---|---|---|---|---|---|
| | 50 | | | | | 55 | | | | | 60 | | | | |

| Ser | Leu | Lys | Val | Glu | Lys | Ile | Leu | Phe | Gln | Gly | Lys | Ser | Asp | Tyr | Gln |
|---|---|---|---|---|---|---|---|---|---|---|---|---|---|---|---|
| 65 | | | | | 70 | | | | | 75 | | | | | 80 |

| Asp | Val | Ile | Val | Phe | Gln | Ser | Ala | Thr | Tyr | Gly | Lys | Val | Leu | Val | Leu |
|---|---|---|---|---|---|---|---|---|---|---|---|---|---|---|---|
| | | | | 85 | | | | | 90 | | | | | 95 | |

| Asp | Gly | Val | Ile | Gln | Leu | Thr | Glu | Arg | Asp | Glu | Cys | Ala | Tyr | Gln | Glu |
|---|---|---|---|---|---|---|---|---|---|---|---|---|---|---|---|
| | | | 100 | | | | | 105 | | | | | 110 | | |

| Met | Ile | Thr | His | Leu | Pro | Leu | Cys | Ser | Ile | Ser | Asn | Pro | Lys | Lys | Val |
|---|---|---|---|---|---|---|---|---|---|---|---|---|---|---|---|
| | | 115 | | | | | 120 | | | | | 125 | | | |

| Leu | Val | Ile | Gly | Gly | Gly | Asp | Gly | Gly | Val | Leu | Arg | Glu | Val | Ala | Arg |
|---|---|---|---|---|---|---|---|---|---|---|---|---|---|---|---|
| | 130 | | | | | 135 | | | | | 140 | | | | |

| His | Ser | Ser | Val | Glu | Gln | Ile | Asp | Ile | Cys | Glu | Ile | Asp | Lys | Met | Val |
|---|---|---|---|---|---|---|---|---|---|---|---|---|---|---|---|
| 145 | | | | | 150 | | | | | 155 | | | | | 160 |

| Val | Asp | Val | Ala | Lys | Gln | Tyr | Phe | Pro | Asn | Val | Ala | Val | Gly | Tyr | Glu |
|---|---|---|---|---|---|---|---|---|---|---|---|---|---|---|---|
| | | | | 165 | | | | | 170 | | | | | 175 | |

| Asp | Pro | Arg | Val | Asn | Leu | Ile | Ile | Gly | Asp | Gly | Val | Ala | Phe | Leu | Lys |
|---|---|---|---|---|---|---|---|---|---|---|---|---|---|---|---|
| | | | 180 | | | | | 185 | | | | | 190 | | |

| Asn | Ala | Ala | Glu | Gly | Thr | Tyr | Asp | Ala | Val | Ile | Val | Asp | Ser | Ser | Asp |
|---|---|---|---|---|---|---|---|---|---|---|---|---|---|---|---|
| | | 195 | | | | | 200 | | | | | 205 | | | |

| Pro | Ile | Gly | Pro | Ala | Lys | Glu | Leu | Phe | Glu | Lys | Pro | Phe | Phe | Glu | Ser |
|---|---|---|---|---|---|---|---|---|---|---|---|---|---|---|---|
| | 210 | | | | | 215 | | | | | 220 | | | | |

| Val | Asn | Arg | Ala | Leu | Arg | Pro | Gly | Gly | Val | Val | Cys | Thr | Gln | Ala | Glu |
|---|---|---|---|---|---|---|---|---|---|---|---|---|---|---|---|
| 225 | | | | | 230 | | | | | 235 | | | | | 240 |

```
Ser Leu Trp Leu His Met Asp Ile Ile Glu Asp Ile Val Ser Asn Cys
                245                 250                 255

Arg Asp Ile Phe Lys Gly Ser Val Asn Tyr Ala Trp Thr Ser Val Pro
            260                 265                 270

Thr Tyr Pro Ser Gly Val Ile Gly Phe Met Leu Cys Ser Ser Glu Gly
        275                 280                 285

Pro Gln Val Asp Phe Lys Lys Pro Val Ser Leu Ile Asp Thr Asp Glu
    290                 295                 300

Ser Ser Ile Lys Ser His Cys Pro Leu Lys Tyr Tyr Asn Ala Glu Ile
305                 310                 315                 320

His Ser Ala Ala Phe Cys Leu Pro Ser Phe Ala Lys Lys Val Ile Asp
                325                 330                 335

Ser Lys Ala Asn
            340

<210> SEQ ID NO 12
<211> LENGTH: 13
<212> TYPE: DNA
<213> ORGANISM: Artificial Sequence
<220> FEATURE:
<223> OTHER INFORMATION: Oligonucleotide sequence from Arapidopsis
      thaliana WT Col-0

<400> SEQUENCE: 12
agatatagaa cat                                                        13

<210> SEQ ID NO 13
<211> LENGTH: 13
<212> TYPE: DNA
<213> ORGANISM: Artificial Sequence
<220> FEATURE:
<223> OTHER INFORMATION: Oligonucleotide sequence from Arabidopsis
      thaliana mutant als7-2

<400> SEQUENCE: 13
agatataaaa cat                                                        13

<210> SEQ ID NO 14
<211> LENGTH: 13
<212> TYPE: DNA
<213> ORGANISM: Artificial Sequence
<220> FEATURE:
<223> OTHER INFORMATION: Oligonucleotide sequence from Arabidopsis
      thaliana WT Col-0

<400> SEQUENCE: 14
gaacaaggta ttg                                                        13

<210> SEQ ID NO 15
<211> LENGTH: 13
<212> TYPE: DNA
<213> ORGANISM: Artificial Sequence
<220> FEATURE:
<223> OTHER INFORMATION: Oligonucleotide sequence from Arabidopsis
      thaliana mutant als7-1

<400> SEQUENCE: 15
gaacaagtta ttg                                                        13
```

METHOD AND COMPOSITIONS TO PROMOTE PLANT GROWTH IN METAL CONTAMINATED ENVIRONMENTS

CROSS REFERENCE TO RELATED APPLICATIONS

This application is a U.S. National Stage Application filed under 35 U.S.C. 371 and claims priority to International Application No. PCT/US12/37165, filed May 9, 2012, which application claims priority to U.S. Provisional Application No. 61/484,007, filed May 9, 2011, the disclosures of which is are incorporated herein by reference.

STATEMENT AS TO GOVERNMENT SPONSORED RESEARCH

This invention was made with Government support under Grant No. 2005-01074 awarded by the U.S. Department of Agriculture. The U.S. Government has certain rights in this invention.

FIELD OF THE INVENTION

The disclosure provides polynucleotides and polypeptide useful to confer metal resistance and fitness to a plant, methods of use in phytoremediation, transgenic plants and recombinant cells thereof.

BACKGROUND

Aluminum (Al) toxicity is a global issue that negatively affects agricultural productivity in acid soil regions, which arguably comprise upwards of 50% of the world's arable land. In acid soil environments, Aluminum speciates to the highly toxic trivalent cation form, $Al^{3+}$. Aluminum toxicity is manifested as severely reduced root growth that causes reduced shoot growth and crop yields. Even though Aluminum toxic soils are widespread, they represent some of the most biologically diverse regions in terms of plant life, indicating that native plants have evolved poorly understood mechanisms that allow them to tolerate levels of Aluminum that are highly inhibitory for agriculturally important crop species.

Aluminum-rich soils are a significant source of crop damage, affecting at least 50% of the world's potentially arable lands. The problem is particularly vital in the tropics, where the need to feed swelling populations is pressing and yet large swathes of arable lands are rendered fallow due to their acidic aluminum-rich compositions. Research into aluminum tolerance in plants seeks to address and overcome these problems by developing crop plants capable of growing despite the presence of toxic levels of aluminum.

SUMMARY

The disclosure provides a method for phytoremediation of soil, groundwater, industrial waste or water contaminated with at least one metal ion selected from the group consisting of aluminum, copper, cobalt, zinc, antimony, mercury, cadmium, arsenate and arsenite, the method comprising the step of contacting a plant with an agent the promotes polyamine synthesis or increases polyamine levels in the plant.

The disclosure also provides a method for phytoremediation of soil, groundwater, industrial waste or water contaminated with at least one metal ion selected from the group consisting of aluminum, copper, cobalt, zinc, antimony, mercury, cadmium, arsenate and arsenite, the method comprising upregulating or expression a heterologous gene in a plant that promotes polyamine synthesis or levels in the plant.

In certain embodiment of the foregoing methods, the metal ion is aluminium ion. In other embodiments, the agent that increases polyamine levels is selected from the group consisting of putrescine, spermidine, spermine, cadaverine or a composition including at least one of these compounds. In specific embodiments, the agent is spermine. In specific embodiments, the agent is applied to the root, soil or leaves of a plant prior to, simultaneously with or following growing the plant in a contaminated soil.

The disclosure provides a method for phytoremediation of soil, groundwater, industrial waste or water contaminated with at least one metal ion selected from the group consisting of aluminum, copper, cobalt, zinc, antimony, mercury, cadmium, arsenate and arsenite, the method comprising the step of contacting a plant with at least one polyamine agent the promotes polyamine synthesis or polyamine levels in the plant.

The disclosure also provides a method for phytoremediation of soil, groundwater, industrial waste or water contaminated with at least one metal ion selected from the group consisting of aluminum, copper, cobalt, zinc, antimony, mercury, cadmium, arsenate and arsenite, the method comprising upregulating polyamine synthesis in a plant or expressing a heterologous polyamine metabolism gene in a plant that promotes polyamine synthesis or levels in the plant, wherein the plant grows more effectively on a contaminate metal environment than a plant lacking polyamine synthesis or having reduced polyamine synthesis compared to a transgenic plant.

The disclosure also provides a method of promoting plant growth on soil, groundwater, industrial waste or water contaminated with at least one metal ion selected from the group consisting of aluminum, copper, cobalt, zinc, antimony, mercury, cadmium, arsenate and arsenite, the method comprising contacting the plant or the plant's environment with at least one polyamine agent wherein the at least one polyamine agent promotes plant growth compared to a plant or environment not contacted with the at least one polyamine agent.

In any of the foregoing the metal ion can be an aluminium ion. In another embodiment of any of the foregoing the at least one polyamine agent that increases polyamine levels is selected from the group consisting of putrescine, spermidine, spermine, cadaverine or a composition including at least one of these compounds. In a further embodiment, the at least one polyamine agent is spermine.

The disclosure also provides a method of growing plants in an environment contaminated with at least one metal ion selected from the group consisting of aluminum, copper, cobalt, zinc, antimony, mercury, cadmium, arsenate and arsenite comprising contacting the environment with (i) a transgenic plant comprising non-natural polyamine synthesis, or (ii) at least one polyamine agent that increases polyamine content of the plant.

In any of the foregoing embodiment, the at least one polyamine agent is at least one compound selected from the group consisting of 1,3-diaminopropane, putrescine, cadaverine, cardine, spermidine, homospermidine, aminopropylcadaverine, termine, spermine, thermospermine, canavalmine, aminopentylnorspermidine, N,N-bis(aminopropyl)cadaverine, homospermine, caldopentamine, homocaldopentamine, caldohexamine, and homocaldohexamine. In a further embodiment of any of the foregoing, the polyamine is at least one compound selected from the group consisting of putrescine, spermidine, and spermine. In yet a further embodiment, the at least one polyamine agent comprises two or more polyamine agents.

The disclosure also provides a composition comprising a polyamine agent for application to a metal contaminate environment. The composition comprises at least one polyamine agent selected from the group consisting of 1,3-diaminopropane, putrescine, cadaverine, cardine, spermidine, homospermidine, aminopropylcadaverine, termine, spermine, thermospermine, canavalmine, aminopentylnorspermidine, N,N-bis(aminopropyl)cadaverine, homospermine, caldopentamine, homocaldopentamine, caldohexamine, and homocaldohexamine.

The details of one or more embodiments of the disclosure are set forth in the accompanying drawings and the description below. Other features, objects, and advantages will be apparent from the description and drawings, and from the claims.

BRIEF DESCRIPTION OF THE DRAWINGS

FIG. 1A-F show physiological characterization of the response of als7-1/swa2-2 roots to Al. Roots of als7-1/swa2-2 are severely Al hypersensitive. Col-0 wt and als7-1/swa2-2 seedlings were grown for 10 d in a soaked gel environment (pH 4.2) that was supplemented with either no or increasing concentrations of $AlCl_3$, after which root length was measured. Mean±SE values were determined from 30 roots of each. T-tests were performed by comparing als7-1/swa2-2 to Col-0 wt from the same treatment. An asterisk indicates that a significant difference was found with P<0.01. The ratio of growth of als7-1/swa2-2 roots compared to Col-0 wt roots was also determined and plotted. B) Roots of als7-1/swa2-2 are severely inhibited by Al in a hydroponic environment. Seedlings of Col-0 wt and als7-1/swa2-2 were grown in the absence or presence of increasing concentrations of $AlCl_3$ in a hydroponic environment (pH 4.2) for 7 d after which root growth was measured. Mean±SE values were determined from 30 roots of each. T-tests were performed by comparing als7-1/swa2-2 to Col-0 wt from the same treatment. An asterisk indicates that a significant difference was found with P<0.01. C) Photographs of Col-0 wt and als7-1/swa2-2 seedlings grown in either the absence of presence of 0.75 mM $AlCl_3$ (pH 4.2). D) Col-0 wt and als7-1/swa2-2 roots have normal induction of callose production following treatment with 25 µM $AlCl_3$ (pH 4.2) in a hydroponic environment. Seedlings were grown hydroponically for 6 d after which they were exposed to either 0 or 25 µM $AlCl_3$ (pH 4.2) for 24 h and subsequently stained with Aniline Blue. Callose production was visualized by fluorescent microscopy. E) als7-1/swa2-2 roots accumulate significantly more Al than those of Col-0 wt. Seedlings were grown in a hydroponic environment (pH 4.2) for 10 d after which they were transferred to hydroponic solution supplemented with either 0 or 25 µM $AlCl_3$ (pH 4.2) for 48 h. Root tissue was subsequently collected for analysis by ICP-OES. F) als7-1/swa2-2 roots show hyperinduction of an Al-inducible gene. Col-0 wt and als7-1/swa2-2 seedlings were grown for 10 days in a hydroponic environment (pH 4.2) after which they were transferred to hydroponic solution supplemented with either 0 or 25 µM $AlCl_3$ (pH 4.2) for 48 h. Root tissue was harvested and total RNA was isolated for Northern analysis with AtALMT1. 18S rDNA was used as a probe to judge loading accuracy.

FIG. 2A-E shows als7-1 is a loss-of-function mutation in SWA2/At1g72440. A) Map-based cloning of als7-1 resulted in the identification of a nucleotide substitution in the splice junction between the 5th exon and subsequent intron of SWA2/At1g72440 (SEQ ID Nos:12, 13, 14 and 15). B) Functional complementation of the als7-1/swa2-2 mutant with a full length wt version of At1g72440 resulted in restoration of wt root growth. Col-0 wt, als7-1/swa2-2, and an als7-1/swa2-2 transgenic line carrying the wt version of At1g72440 were grown in a soaked gel environment (pH 4.2) supplemented with 0.75 mM AlCl3. Photograph was taken after 10 d of growth. C) A novel allele, als7-2/swa2-3, was identified by TILLING, after which homozygous seedlings were compared with Col-0 wt and als7-1/swa2-2 for its capability to grow in a soaked gel environment (pH 4.2) supplemented with 0.75 mM $AlCl_3$. Photograph was taken after 10 d of growth. D) Predicted primary structure of the SWA2 protein (SEQ ID NO:7). Amino acids highlighted in blue represent a predicted armadillo-like fold that binds to large substrates in other proteins, with the internal region highlighted in black representing a predicted domain found in CCAAT-binding proteins. Amino acids highlighted in red comprise a putative nuclear localization signal. The amino acid substitution that arises from the als7-2/swa2-3 mutation is outlined in a white box. E) Northern analysis of SWA2 expression. Total RNA was isolated from roots of Col-0 wt and als7-1/swa2-2 that were grown hydroponically in the absence or presence of 25 µM AlCl3 (pH 4.2), after which expression of SWA2 was determined by Northern analysis. Total RNA was also isolated from untreated Col-0 wt leaves, stems, and flowers for Northern analysis with SWA2. 18S rDNA was used as a probe to judge loading accuracy.

FIG. 3A-H shows SWA2 is localized to the nucleolus of the root tip. Analysis of a PROSWA2:SWA2:GFP transgenic line shows that SWA2 is localized to nucleoli of cells of the root tip. A) Closeup view of cells of the root tip of a PROSWA2:SWA2:GFP transgenic line showing GFP fluorescence in nucleoli. For this analysis, DAPI staining was used to show location of the nucleus within the cell. B) Fluorescent and bright field images showing location of SWA2 in untreated roots of a PROSWA2:SWA2:GFP transgenic line. C) Fluorescent and bright field images showing SWA2 localization in the root tip following growth for 2 d in the presence of 25 µM $AlCl_3$ (pH 4.2) in a hydroponic environment. D) Closeup view of the area behind the root tip of an untreated PROSWA2:SWA2:GFP transgenic line. E)-H) Survey of areas along the length of the root of an untreated PROSWA2:SWA2:GFP transgenic line showing that expression of SWA2 is coincident with areas that develop into lateral roots, which are indicated by a white arrow.

FIG. 4A-C shows als7-1/swa2-2 roots have reduced expression of AtARD3 following Al treatment. Preliminary microarray analysis revealed that the als7-1/swa2-2 mutation leads to reduced expression of a subset of genes in roots following Al exposure. A) Northern analysis for expression of AtARD3 in roots of Col-0 wt and als7-1/swa2-2. Based on this preliminary microarray analysis, als7-1/swa2-2 roots have reduced expression of both AtARD3 and At4g10500 following exposure to Al. 10 d old roots of seedlings of Col-0 wt and als7-1/swa2-2 were exposed for 24 h to either 0 or 25 µM $AlCl_3$ (pH 4.2) in a hydroponic environment after which total RNA was isolated for Northern analysis to determine expression levels of AtARD3 and At4g10500. 18S rDNA was used as a probe to judge loading accuracy. B) qPCR analysis was performed to compare expression levels of AtARD3 and At4g10500 between Al-treated roots of Col-0 wt and als7-1/swa2-2. Expression levels were standardized based on expression levels of ACTIN2. C) Supplementation of als7-1/swa2-2 roots with L-methionine partly restores growth for mutant roots in the presence of Al. Seedlings of Col-0 wt and als7-1/swa2-2 were grown in a soaked gel environment either in the absence or presence of 0.75 mM $AlCl_3$ (pH 4.2) with or without 10 μM L-methionine. After 7 d growth, root length was measured for all treatments, with mean±SE values determined from 30 roots of each.

FIG. 5A-D shows Endogenous polyamines are required for Al resistance in *Arabidopsis* roots. A) Roots of als7-1/swa2-2 have reduced spermine content. Seedlings of Col-0 wt and als7-1/swa2-2 were grown for 7 d hydroponically either in the absence or presence 25 μM $AlCl_3$ (pH 4.2), after which root tissue was collected for analysis of spermine content by HPLC. B) Supplementation of growth media with spermine increases root growth in the presence of Al. Seedlings of Col-0 wt and als7-1/swa2-2 were grown in a hydroponic environment either in the absence or presence of 25 μM $AlCl_3$ (pH 4.2) with or without 25 μM spermine. After 7 d growth, root length was measured for all treatments, with mean±SE values determined from 30 roots of each. C) Treatment of Col-0 wt seedlings with an inhibitor of spermine biosynthesis, DFMO, reduces root growth in the presence of Al. Seedlings of Col-0 wt were grown either in the absence or presence of 1.5 mM DEMO in a hydroponic environment supplemented with increasing concentrations of $AlCl_3$ (pH 4.2). After 7 d, root length was measured for all treatments, with mean±SE values determined from 30 roots of each. D) Spermine treatment reduces Al uptake. Seedlings of Col-0 wt were grown hydroponically either in the absence or presence of 25 μM spermine for 5 d after which the samples were transferred to a solution with or without 25 μM $AlCl_3$ (pH 4.2) containing either 0 or 25 μM spermine. Following 2 d of growth, root tissue was collected and treated for measurement of Al content by ICP-OES.

DETAILED DESCRIPTION

As used herein and in the appended claims, the singular forms "a," "and," and "the" include plural referents unless the context clearly dictates otherwise. Thus, for example, reference to "a polynucleotide" includes a plurality of such polynucleotides and reference to "the peptide" includes reference to one or more peptides, and so forth.

Unless defined otherwise, all technical and scientific terms used herein have the same meaning as commonly understood to one of ordinary skill in the art to which this disclosure belongs. Although methods and materials similar or equivalent to those described herein can be used in the practice of the disclosed methods and compositions, the exemplary methods, devices and materials are described herein.

Also, the use of "or" means "and/or" unless stated otherwise. Similarly, "comprise," "comprises," "comprising" "include," "includes," and "including" are interchangeable and not intended to be limiting.

It is to be further understood that where descriptions of various embodiments use the term "comprising," those skilled in the art would understand that in some specific instances, an embodiment can be alternatively described using language "consisting essentially of" or "consisting of."

Any publications discussed above and throughout the text are provided solely for their disclosure prior to the filing date of the present application. Nothing herein is to be construed as an admission that the inventors are not entitled to antedate such disclosure by virtue of prior disclosure.

In recent years, Al toxicity has garnered significant attention due to several advances in the understanding of mechanisms of both Al resistance and tolerance. While not only giving insights into how plants deal with Al toxicity, these findings have resulted in strategies for improving the capability of crops to grow in Al containing acid soils. This is particularly important, since unlike other soil issues such as heavy metal contamination, it is not possible to remediate Al due to its naturally occurring abundance. Al resistance in crops has been attributed to increased capability to release Al-chelating organic acids into the rhizosphere, with this being dependent on higher expression levels of the various transporters that are responsible for exudation. As far as Al tolerance, a model is evolving in which root growth inhibition is an active process by which DNA damage checkpoints actively halt root growth following detection of Al-dependent damage. It is not clear whether either of these mechanisms accounts for the wide range of variation seen in natural populations with regard to growth in Al toxic environments.

Al toxicity has been predicted to be extremely complex due to the large number of sites of Al binding, which arguably represent any anionic extra- or intracellular site. Because of the complexity, it has been suggested that Al tolerance cannot be enhanced through single site changes since such changes would, at best, lead to minimal incremental increases in tolerance. Surprisingly, it appears that Al-dependent root growth inhibition in *Arabidopsis* in large part results from an active mechanism that arrests cell cycle progression in the root tip in response to an as yet undefined form of Al-dependent DNA damage. Mutational loss of a component of the mechanism required for detecting and responding to this damage leads to a substantive increase in root growth in the presence of levels of Al that normally are severely inhibitory to root growth.

Al resistance mechanisms effectively represent those that allow plants to limit the internalization of Al primarily through exclusion. The most well studied Al exclusion mechanism is dependent on release of $Al^{3+}$-chelating di- and tricarboxylic acids that are speculated to bind to Al and prevent it from being internalized. For example, Al-resistant cultivars of wheat, maize, barley, and sorghum release increased levels of either malate or citrate in an Al-responsive manner. In recent years, intensive efforts led to the isolation of several active transporters that are responsible for this Al-inducible release of organic acids including wheat ALMT1, *Arabidopsis* AtALMT1, sorghum AltSB, and barley HvAACT1. While a loss-of-function mutation in AtALMT1 in *Arabidopsis* leads to severe Al hypersensitivity, overexpression of several of these organic acid transporters in various plant systems leads to measurable increases in Al resistance.

Another speculated mechanism for Al resistance is rhizosphere alkalinization, since Al toxicity is directly dependent on the pH of the growth environment. While not demonstrated in an agricultural model system, mutational analysis of *Arabidopsis* did result in the identification of a mutant line with increased growth in the presence of Al resulting from an increased capability to raise the pH of the growth medium. It is likely that by altering nutrient uptake mechanisms, plants could be engineered to raise rhizosphere pH, which would force Al to speciate to less toxic forms.

Finally, there has been limited evidence that modification of extra- and intracellular anionic sites can have a positive impact on Al resistance. This mechanism is speculated to be dependent on increased production of cationic compounds that effectively compete with $Al^{3+}$ for binding to negative sites that are commonly found in the cell wall, at the cell membrane, and throughout the cell.

The methods and compositions of the disclosure useful for treating plants grown on metal toxic soils and water (e.g., Al toxic environments) were identified through the analysis of a loss-of-function SLOW WALKER 2 (swa2) mutant. This study was an important advance in the understanding of Al resistance since this represents the first genetic evidence that altered polyamine content has a direct relationship to the capability of roots to grow in an Al toxic environment. In plants, polyamines have been found to be required for response to various abiotic and biotic stresses. For example, endogenous putrescine is necessary for stress tolerance since a loss-of-function *Arabidopsis* mutant affecting arginine decarboxylase (ADC2), which is the enzyme responsible for putrescine biosynthesis, has increased sensitivity to salinity.

The disclosure demonstrates a causal relationship between reduced polyamine content and decreased Al resistance as measured by Al-dependent root growth inhibition, Al uptake, and Al-responsive gene expression. This has been achieved both through mutational loss of a factor necessary for the maintenance of normal polyamine levels and by a pharmacological approach that is a well accepted method for inhibition of polyamine biosynthesis. The disclosure also demonstrates that supplementation of roots with exogenous spermine results in a substantial increase in root growth compared to control roots. Although not required to indicate a mechanism of action, and not wishing to be bound by such, the benefit of polyamine treatment are likely dependent on competition between polyamines and $Al^{3+}$ for binding to negatively charged sites within the root. Possible extracellular sites include the cell wall and plasma membrane, both of which are well-documented targets of $Al^{3+}$ due to a preponderance of anionic sites in these regions. Intracellular sites are also expected to be numerous, since $Al^{3+}$ is expected to bind to any negatively charged target. Likely though, spermine and other polyamines compete with $Al^{3+}$ for binding at the cell surface since polyamine treatment is clearly associated with a significant reduction in Al accumulation, which cannot be explained by modification of internal $Al^{3+}$ targets by polyamines. Regardless of the mechanism by which polyamines enhance Al resistance, the work here demonstrates that endogenous polyamines play a critical role in mediating Al resistance and thus altering (e.g., increasing) polyamine content in roots is an effective strategy for improving crop productivity in Al toxic environments or other environments with trivalent metal contamination.

The disclosure demonstrates that reduced capability to produce polyamines leads to increased Al sensitivity in conjunction with increased Al uptake, with the observed Al hypersensitivity being reversed by addition of exogenous polyamines (e.g., spermine). Accordingly, the disclosure provides a method to wherein increasing endogenous or addition of exogenous polyamines is an effective means by which to improve Al resistance in agriculturally important crops.

The disclosure provides genetic evidence for a novel mechanism for Al resistance that depends on endogenous or exogenous polyamines, such as spermine, which functions to reduce the amount of Al that accumulates within root tissue. The disclosure demonstrates that supplementation of roots with exogenous spermine is an effective strategy for increasing Al resistance in roots.

In yet another embodiment, the disclosure provides agents useful for promoting plant growth on aluminum contaminated soils. The method comprises contacting the soil or plant with a biocompatible polyamine.

A "polyamine" as used in the disclosure is a generic name for aliphatic hydrocarbons having two or more primary amino groups, which are natural substances universally present in living things. Twenty or more polyamines have been found: for example, 1,3-diaminopropane, putrescine, cadaverine, cardine, spermidine, homospermidine, aminopropylcadaverine, termine, spermine, thermospermine, canavalmine, aminopentylnorspermidine, N,N-bis(aminopropyl)cadaverine, homospermine, caldopentamine, homocaldopentamine, caldohexamine, and homocaldohexamine. Representative polyamines are putrescine, spermidine, and spermine.

"Putrescine" is one of the representative polyamines, a general natural substance universally present in living things, and an aliphatic hydrocarbon compound having two primary amino groups. "Spermidine" is one of representative polyamines, a general natural substance universally present in living things, and an aliphatic hydrocarbon compound having three primary amino groups. "Spermine" is one of representative polyamines, a general natural substance universally present in living things, and an aliphatic hydrocarbon compound having four primary amino groups.

Polyamines suitable in the methods of the disclosure can be any biocompatible polyamine as described above. In certain embodiment, the polyamine is selected from the group consisting of putrescine, spermidine, spermine, cadaverine or a composition including at least one, two, three or more of these compounds.

Methods are provided for growing a plant on a metal toxic environment, such as an aluminum toxic environment or inhibiting metal toxicity to a plant comprising applying or contacting a plant with an effective amount of a composition comprising a polyamine or derivative thereof. "Effective amount" is intended to mean an amount sufficient to inhibit metal toxicity (e.g., aluminum toxicity) and/or promote plant growth on a metal toxic environment such as an aluminum contaminated environment. A metal toxic or aluminum toxic environment refers to an environment for plant growth wherein the metal content (e.g., the trivalent metal ions of the environment) have a negative impact on plant growth and/or survival.

The compositions of the disclosure include a polyamine or derivative thereof and may further include a surface-active agent, an inert carrier, a preservative, a humectant, a feeding stimulant, an attractant, an encapsulating agent, a binder, an emulsifier, a dye, a UV protective, a buffer, a flow agent or fertilizers, micronutrient donors, or other preparations that influence plant growth. One or more agrochemicals including, but not limited to, herbicides, insecticides, fungicides, bactericides, nematicides, molluscicides, acaracides, plant growth regulators, harvest aids, and fertilizers, can be combined with carriers, surfactants or adjuvants customarily employed in the art of formulation or other components to facilitate product handling and application for particular plants. Suitable carriers and adjuvants can be solid or liquid and correspond to the substances ordinarily employed in formulation technology, e.g., natural or regenerated mineral substances, solvents, dispersants, wetting agents, tackifiers, binders, or fertilizers. The active ingredients of the disclosure are normally applied in the form of compositions and can be applied to the crop area, plant, or seed to be treated or in the case of cuttings (e.g., cut flowers) to the water. For example, the compositions of the disclosure may be applied during growth, seeding or storage.

The polyamine or derivative thereof of the disclosure may be applied simultaneously or in succession with other compounds. Methods of applying a composition of the disclosure include, but are not limited to, foliar application, seed coating, and soil or water application. The number of applications and the rate of application depend on the particular purpose and plant to inhibit toxicity or promote growth on a planned toxic environment.

Suitable surface-active agents that may be combined with the polyamine or derivatives include, but are not limited to, anionic compounds such as a carboxylate of, for example, a metal; carboxylate of a long chain fatty acid; an N-acylsarcosinate; mono or di-esters of phosphoric acid with fatty alcohol ethoxylates or salts of such esters; fatty alcohol sulfates such as sodium dodecyl sulfate, sodium octadecyl sulfate or sodium cetyl sulfate; ethoxylated fatty alcohol sulfates; ethoxylated alkylphenol sulfates; lignin sulfonates; petroleum sulfonates; alkyl aryl sulfonates such as alkylbenzene sulfonates or lower alkylnaphtalene sulfonates, e.g., butyl-naphthalene sulfonate; salts of sulfonated naphthalene-formaldehyde condensates; salts of sulfonated phenol-formaldehyde condensates; more complex sulfonates such as the amide sulfonates, e.g., the sulfonated condensation product of oleic acid and N-methyl taurine; or the dialkyl sulfosuccinates, e.g., the sodium sulfonate or dioctyl succinate. Non-ionic agents include condensation products of fatty acid esters, fatty alcohols, fatty acid amides or fatty-alkyl- or alkenyl-substituted phenols with ethylene oxide, fatty esters of polyhydric alcohol ethers, e.g., sorbitan fatty acid esters, condensation products of such esters with ethylene oxide, e.g., polyoxyethylene sorbitar fatty acid esters, block copolymers of ethylene oxide and propylene oxide, acetylenic glycols such as 2,4,7,9-tetraethyl-5-decyn-4,7-diol, or ethoxylated acetylenic glycols. Examples of a cat-ionic surface-active agent include, for instance, an aliphatic mono-, di-, or polyamine such as an acetate, naphthenate or oleate; or oxygen-containing amine such as an amine oxide of polyoxyethylene alkylamine; an amide-linked amine prepared by the condensation of a carboxylic acid with a di- or polyamine; or a quaternary ammonium salt.

Examples of inert materials that can be combined with a polyamine or derivative include, but are not limited to, inorganic minerals such as kaolin, phyllosilicates, carbonates, sulfates, phosphates, or botanical materials such as cork, powdered corncobs, peanut hulls, rice hulls, and walnut shells.

The compositions of the disclosure can be in a suitable form for direct application or as a concentrate of primary composition that requires dilution with a suitable quantity of water or other diluent before application. The concentration of the polyamine or derivative thereof will vary depending upon the nature of the particular formulation, specifically, whether it is a concentrate or to be used directly.

A composition of the disclosure can be applied to the environment of a plant, for example, spraying, atomizing, dusting, scattering, coating or pouring, introducing into or on the soil, introducing into irrigation water, by seed treatment or general application or dusting. The compositions of the disclosure can conveniently contain an insecticide if this is thought necessary.

As used above, and elsewhere herein, the term "plant" refers to either a whole plant, a plant part, a plant cell, or a group of plant cells, such as plant tissue, for example. Plantlets are also included within the meaning of "plant". Plants include flowering, decorative plants, agricultural plant and the like.

Examples of monocotyledonous plants include, but are not limited to, asparagus, field and sweet corn, barley, wheat, rice, sorghum, onion, pearl millet, rye and oats. Examples of dicotyledonous plants include, but are not limited to tomato, tobacco, cotton, potato, rapeseed, field beans, soybeans, peppers, lettuce, peas, alfalfa, clover, cole crops or *Brassica oleracea* (e.g., cabbage, broccoli, cauliflower, brussels sprouts), radish, carrot, beets, eggplant, spinach, cucumber, squash, melons, cantaloupe, sunflowers and various ornamentals. Woody species include poplar, pine, sequoia, cedar, oak, etc.

In addition, to exogenous application of polyamines, the disclosure provide methods and composition for elevation of internal levels of polyamines through a transgenic approach as an effective strategy for increasing Al resistance of agricultural crops.

In another embodiment, transgenic plants comprising a recombinant pathway promoting S-adenosylmethionine recycling can be used on metal toxic environments (e.g., aluminum environments).

The transgenic metal-resistant plants of the disclosure are useful in the phytoremediation and/or revegetation of soils contaminated with metals. The plants of the disclosure can be grown in soil or aquaculture, with contaminated water or waste water comprising aluminum.

The transgenic plants of the disclosure comprise recombinant polyamine metabolism genes. As used in the a, "polyamine metabolism gene" is a gene coding for a polypeptide or enzyme involved in polyamine biosynthesis in plants. Examples which include arginine decarboxylase (ADC) and ornithine decarboxylase (ODC) genes for the typical polyamine putrescine, S-adenosylmethionine decarboxylase (SAMDC) and spermidine synthase (SPDS) genes for spermidine, and S-adenosylmethionine decarboxylase (SAMDC) and spermine synthase (SPMS) genes for spermine.

For example, Acireductone dioxygenase 3 (AtARD3) is one of four members of the *Arabidopsis* ARD family, members of which are required for methionine salvage and SAM recycling. L-Methionine salvage is critical for normal plant growth and development due to the high demand for SAM in metabolic pathways such as ethylene and polyamine biosyntheses. Each of these biosynthetic pathways results in the formation of methylthioadenosine (MTA) as a by-product that can be recycled through the ARD dependent methionine cycle for regeneration of SAM. In the als7-1/swa2-2 mutant, AtARD3 expression was severely reduced following Al treatment, suggesting an impaired capability to recycle L-methionine and consequently, SAM. When Col-0 wt and als7-1/swa2-2 were grown on low levels of L-methionine, there was a dramatic increase in root length of als7-1/swa2-2 only in the presence of $AlCl_3$. Since biosynthesis of spermidine and spermine require a pool of available SAM and since addition of exogenous methionine had a positive effect on the Al dependent growth defect of als7-1/swa2-2, promoting the production of polyamines using heterologous genes can improve growth on metal contaminated environments.

Arginine decarboxylase (ADC: EC4.1.1.19.) is an enzyme catalyzing the reaction producing agmatine and carbon dioxide from L-arginine. Ornithine decarboxylase (ODC: EC4.1.1.17.) is an enzyme catalyzing putrescine and carbon dioxide from L-ornithine. S-adenosylmethionine decarboxylase (SAMDC: EC4.1.1.50.) is an enzyme catalyzing the reaction producing adenosylmethylthiopropylamine and carbon dioxide from S-adenosylmethionine. Spermidine synthase (SPDS: EC2.5.1.16.) is an enzyme catalyzing the reaction producing spermidine and methylthioadenosine from putrescine and adenosylmethylthiopropylamine. Spermine synthase (SEQ ID NO:8 and 9) produces spermine.

These genes, any of which may be derived, can be isolated from various plants. Specific examples include dicotyledons such as Cucurbitaceae; Solanaceae; Brassicaceae such as *Arabidopsis thaliana*; Papilionaceae such as alfalfa and *Vigna unguiculata*; Malvaceae; and Asteraceae; or monocotyledons such as gramineae, including wheat, barley, and corn. Drought-resistant cactus or Mesembryanthemum crystallinum are also included.

Plant tissue in which the plant-derived polyamine metabolism genes of the disclosure are isolated may be in the form of seeds or in the process of growing. The genes may be isolated from part or all of the tissue of growing plants. Any part can be used to isolate genes, but whole plants, buds, flowers, ovaries, fruit, leaves, stems, roots, and the like. Parts that are tolerant to environmental stress are especially desirable.

The sequences of the foregoing genes are well known in the art (see, e.g., U.S. Patent Publ. No. 20100083401, the disclosure of which is incorporated herein by reference).

The transgenic plants of the disclosure are obtained by the transformation of cells of plants lacking the polyamine metabolisms gene(s) or are engineered to over express a polyamine metabolism gene. Such methods include transforming a plant cell with an expression vector containing the exogenous polyamine metabolism gene under the control of a promoter capable of functioning in plants.

Examples of promoters capable of functioning in plants include the 35S promoter of the cauliflower mosaic virus (CaMV) which is structurally expressed in plant cells, the nopaline synthase gene (NOS) promoter, octopine synthase gene (OCS) promoter, phenylalanine ammonia lyase (PAL) gene promoter, and chalcone synthase (CHS) gene promoter. Other well-known plant promoters are known in the art.

Promoters other than constitutive promoters can be used and include promoters regulated by low temperature, elevated temperature, stress, drought, light, heat, hormones, damage or the like can be used to express the target gene according to the living environment.

An organ- or tissue-specific promoter can also be used to express the target gene only in specific organs or tissue.

The exogenous polyamine metabolism gene in an expression vector of the disclosure is located downstream of the promoter so that transcription is controlled by the promoter capable of functioning in plants. A transcription termination signal (terminator region) capable of functioning in plants should also be added downstream of the polyamine metabolism gene.

An expression vector of the disclosure may also contain a cis-regulatory element such as an enhancer sequence. The expression vector may also contain a marker gene for selecting transformants such as a drug-resistance gene marker, examples of which include the neomycin phosphotransferase II (NPTII) gene, the phosphinothricin acetyl transferase (PAT) gene, and the glyophosate resistance gene. It is advantageous to ensure that a herbicide resistance gene is also present on the vector so that the use of a herbicide during cultivation will result in conditions involving selection pressure.

To facilitate mass production and purification, the expression vector should also contain a selection marker gene (such as ampicillin resistance gene or tetracycline resistance gene) in *E. coli* and a replication origin capable of autonomous replication in *E. coli*. The expression vector of the disclosure can be constructed in a simple manner by inserting the selection marker gene as needed and an expression cassette of the polyamine metabolism-related enzyme gene at the cloning site of an *E. coli* vector (pUC or pBR series).

When the exogenous polyamine metabolism gene is introduced by infection with *Agrobacterium tumefaciens* or *Agrobacterium* rhizogenes, the polyamine metabolism gene expression cassette can be inserted in the T-DNA region on a Ti or Ri plasmid of the cells. At present, binary vector systems are used in standard methods of transformation with *Agrobacterium*. The necessary functions for T-DNA transfer are independently provided by both the T-DNA itself and the Ti (or Ri) plasmid, these structural elements being divided on separate vectors. The binary plasmid has 25 by border sequences at both ends necessary for cleaving and combining the T-DNA, and the plant hormone gene inducing crown gall (or hairy root) is removed, simultaneously providing room for inserting the exogenous gene. Examples of commercially available binary vectors include pBI101 and pBI121 (both by Clontech). The Vir region involved in the incorporation of the T-DNA has trans action on the separate Ti (or Ri) plasmid referred to as the helper plasmid.

Various conventionally methods can be used for the transformation of the plants. Examples include the PEG method in which protoplasts are isolated from plant cells by treatment with a cell wall-degrading enzyme such as cellulase or hemicellulase, and polyethylene glycol is added to a suspension of the protoplasts and an expression vector containing the aforementioned polyamine metabolism gene expression cassette to incorporate the expression vector into the protoplasts by a process such as endocytosis; the liposome method in which an expression vector is introduced by ultrasonic treatment or the like into lipid membrane vesicles such as phosphatidylcholine, and the vesicles are fused with protoplasts in the presence of PEG; methods of fusion in a similar process using micelles; and electroporation in which electrical pulses are applied to a suspension of protoplasts and an expression vector to incorporate the vectors in the external solution into the protoplasts. Processes for introducing the gene into intact cells with cell walls include direct injection such as microinjection in which a micropipette is inserted into cells to inject the vector DNA in the pipettes under hydraulic or gas pressure into the cells, or the particle gun method in which metal microparticles coated with DNA are accelerated through the detonation of an explosive or gas pressure and thus introduced into the cells, and methods involving the use of infection with *Agrobacterium*. A convenient method such as the *Agrobacterium* method and the particle gun method can also be used. The particle gun method is useful in that genes can be directly introduced into the apical meristem of plants while cultivated. In the *Agrobacterium* method, the genomic DNA of a plant virus such as the tomato golden mosaic virus (TGMV) or another gemini virus is simultaneously inserted between the border sequences into the binary vector, so that the viral infection can spread throughout the entire plant and the target gene can be simultaneously introduced into the entire plant simply by inoculating cells at any location of the cultivated plant with the viral cell suspension.

It will be recognized that the genes identified above are not limiting and that modified sequences that encode an enzyme for the production of a polyamine can be used. Such modified polynucleotides are sometimes termed "variants" and can include modifications that include silent mutations or that result in codons that produce conservative substitutions at a particular amino acid position of the encoded polypeptide. For example, a polynucleotide that hybridizes under moderate to high stringency to a gene encoding a polyamine metabolism enzyme which is not 100% identical to the native polyamine gene are encompassed by the disclosure. The polynucleotide that hybridizes, although not 100% identical, encodes a polyamine metabolism enzyme. As used herein, moderate to high stringency conditions for hybridization are conditions which achieve the same, or about the same, degree of specificity of hybridization as the conditions employed by the current inventors. An example of high stringency conditions are hybridizing at 68° C. in 5×SSC/5×Denhardt's solution/0.1% SDS, and washing in 0.2×SSC/0.1% SDS at room temperature. An example of conditions of moderate stringency are hybridizing at 68° C. in 5×SSC/5×Denhardt's solution/0.1% SDS and washing at 42° C. in 3×SSC. The parameters of temperature and salt concentration can be varied to achieve the desired level of sequence identity between probe and target nucleic acid. See, e.g., Sambrook et al. (1989) vide infra or Ausubel et al. (1995) Current Protocols in Molecular Biology, John Wiley & Sons, New York, N.Y., for further guidance on hybridization conditions.

A "heterologous" nucleic acid construct or sequence has a portion of the sequence that is not native to the plant cell in which it is expressed. Heterologous, with respect to a control sequence refers to a control sequence (i.e. promoter or enhancer) that does not function in nature to regulate the same gene the expression of which it is currently regulating. Generally, heterologous nucleic acid sequences are not endogenous to the cell or part of the genome in which they are present, and have been added to the cell, by infection, transfection, microinjection, electroporation, or the like. A "heterologous" nucleic acid construct may contain a control sequence/DNA coding sequence combination that is the same as, or different from a control sequence/DNA coding sequence combination found in the native plant.

As used herein, the term "gene" means the segment of DNA involved in producing a polypeptide chain, which may or may not include regions preceding and following the coding region, e.g., at 5' untranslated (5' UTR) or "leader" sequences and/or 3' UTR or "trailer" sequences, as well as intervening sequences (introns) between individual coding segments (exons) and non-transcribed regulatory sequence.

As used herein, the term "gene expression" refers to the process by which a polypeptide is produced based on the nucleic acid sequence of a gene. The process includes both transcription and translation; accordingly, "expression" may refer to either a polynucleotide or polypeptide sequence, or both. Sometimes, expression of a polynucleotide sequence will not lead to protein translation. "Over-expression" refers to increased expression of a polynucleotide and/or polypeptide sequence relative to its expression in a wild-type or other plant and may relate to a naturally-occurring or non-naturally occurring sequence. "Ectopic expression" refers to expression at a time, place, and/or increased level that does not naturally occur in the non-altered or wild-type plant. "Under-expression" refers to decreased expression of a polynucleotide and/or polypeptide sequence, generally of an endogenous gene, relative to its expression in a wild-type plant. The terms "mis-expression" and "altered expression" encompass over-expression, under-expression, and ectopic expression.

The term "introduced" in the context of inserting a polynucleotide into a cell, means "transfection", or "transformation" or "transduction" and includes reference to the incorporation of a polynucleotide into a eukaryotic or prokaryotic cell where the polynucleotide may be incorporated into the genome of the cell (for example, chromosome, plasmid, plastid, or mitochondrial DNA), converted into an autonomous replicon, or transiently expressed (for example, transfected mRNA).

As used herein, a "plant cell" refers to any cell derived from a plant, including cells from undifferentiated tissue (e.g., callus) as well as plant seeds, pollen, progagules and embryos. The disclosure encompasses modified plants and plant compositions including whole plants, shoot vegetative organs/structures (e.g., leaves, stems and tubers), roots, flowers and floral organs/structures (e.g., bracts, sepals, petals, stamens, carpels, anthers and ovules), seed (including embryo, endosperm, and seed coat) and fruit (the mature ovary), plant tissue (e.g., vascular tissue, ground tissue, and the like) and cells (e.g., guard cells, egg cells, and the like), and progeny of same. The class of plants that can be used in the method of the disclosure is generally as broad as the class of higher and lower plants amenable to transformation techniques, including angiosperms (monocotyledonous and dicotyledonous plants), gymnosperms, ferns, horsetails, psilophytes, lycophytes, bryophytes, and multicellular algae. "Plant tissue" includes differentiated and undifferentiated tissues or plants, including but not limited to roots, stems, shoots, leaves, pollen, seeds, tumor tissue and various forms of cells and culture such as single cells, protoplast, embryos, and callus tissue. The plant tissue may be in plants or in organ, tissue or cell culture.

The disclosure is not limited to any plant species. Plants species contemplated include, but are not limited to, alfalfa, aster, barley, begonia, beet, canola, cantaloupe, carrot, chrysanthemum, clover, corn, cotton, cucumber, delphinium, grape, lawn and turf grasses, lettuce, pea, peppermint, rice, rutabaga, sorghum, sugar beet, sunflower, tobacco, tomatillo, tomato, turnip, wheat, and zinnia.

As used herein, the terms "native" and "wild-type" relative to a given plant trait or phenotype refers to the form in which that trait or phenotype is found in the same variety of plant in nature.

As used herein, the term "modified" regarding a plant trait, refers to a change in the phenotype of a transgenic plant relative to the similar non-transgenic plant. An "interesting phenotype (trait)" with reference to a transgenic plant refers to an observable or measurable phenotype demonstrated by a T1 and/or subsequent generation plant, which is not displayed by the corresponding non-transgenic (i.e., a genotypically similar plant that has been raised or assayed under similar conditions). An interesting phenotype may represent an improvement in the plant or may provide a means to produce improvements in other plants. An "improvement" is a feature that may enhance the utility of a plant species or variety by providing the plant with a unique and/or novel quality.

A "protein" or "polypeptide", which terms are used interchangeably herein, comprises one or more chains of chemical building blocks called amino acids that are linked together by chemical bonds called peptide bonds. A "native" or "wild-type" protein, enzyme, polynucleotide, gene, or cell, means a protein, enzyme, polynucleotide, gene, or cell that occurs in nature.

An "amino acid sequence" is a polymer of amino acids (a protein, polypeptide, etc.) or a character string representing an amino acid polymer, depending on context. The terms "protein," "polypeptide," and "peptide" are used interchangeably herein.

"Conservative amino acid substitution" or, simply, "conservative variations" of a particular sequence refers to the replacement of one amino acid, or series of amino acids, with essentially identical amino acid sequences. One of skill will recognize that individual substitutions, deletions or additions which alter, add or delete a single amino acid or a percentage of amino acids in an encoded sequence result in "conservative variations" where the alterations result in the deletion of an amino acid, addition of an amino acid, or substitution of an amino acid with a chemically similar amino acid.

Conservative substitution tables providing functionally similar amino acids are well known in the art. For example, one conservative substitution group includes Alanine (A), Serine (S), and Threonine (T). Another conservative substitution group includes Aspartic acid (D) and Glutamic acid (E). Another conservative substitution group includes Asparagine (N) and Glutamine (Q). Yet another conservative substitution group includes Arginine (R) and Lysine (K). Another conservative substitution group includes Isoleucine, (I) Leucine (L), Methionine (M), and Valine (V). Another conservative substitution group includes Phenylalanine (F), Tyrosine (Y), and Tryptophan (W).

Thus, "conservative amino acid substitutions" of a listed polypeptide of the disclosure include substitutions of a percentage, typically less than 10%, of the amino acids of the polypeptide, with a conservatively selected amino acid of the same conservative substitution group. Accordingly, a conservatively substituted variation of a polypeptide of the disclosure can contain 100, 75, 50, 25, or 10 substitutions with a conservatively substituted variation of the same conservative substitution group.

It is understood that the addition of sequences which do not alter the activity of a polypeptide encoded by a particular polynucleotide, such as the addition of a non-functional or non-coding sequence, is a conservative variation of the basic polynucleotide.

One of skill in the art will appreciate that many conservative variations of the nucleic acid constructs which are disclosed yield a functionally identical construct. For example, as discussed above, owing to the degeneracy of the genetic code, "silent substitutions" (i.e., substitutions in a nucleic acid sequence which do not result in an alteration in an encoded polypeptide) are an implied feature of every nucleic acid sequence which encodes an amino acid. Similarly, "conservative amino acid substitutions," in one or a few amino acids in an amino acid sequence are substituted with different amino acids with highly similar properties, are also readily identified as being highly similar to a disclosed construct. Such conservative variations of each disclosed sequence are a feature of the polypeptides provided herein.

"Conservative variants" are proteins or enzymes in which a given amino acid residue has been changed without altering overall conformation and function of the protein or enzyme, including, but not limited to, replacement of an amino acid with one having similar properties, including polar or non-polar character, size, shape and charge. Amino acids other than those indicated as conserved may differ in a protein or enzyme so that the percent protein or amino acid sequence similarity between any two proteins of similar function may vary and can be, for example, at least 30%, at least 50%, at least 70%, at least 80%, or at least 90%, as determined according to an alignment scheme. As referred to herein, "sequence similarity" means the extent to which nucleotide or protein sequences are related. The extent of similarity between two sequences can be based on percent sequence identity and/or conservation. "Sequence identity" herein means the extent to which two nucleotide or amino acid sequences are invariant. "Sequence alignment" means the process of lining up two or more sequences to achieve maximal levels of identity (and, in the case of amino acid sequences, conservation) for the purpose of assessing the degree of similarity. Numerous methods for aligning sequences and assessing similarity/identity are known in the art such as, for example, the Cluster Method, wherein similarity is based on the MEGALIGN algorithm, as well as BLASTN, BLASTP, and FASTA (Lipman and Pearson, 1985; Pearson and Lipman, 1988). When using all of these programs, the preferred settings are those that results in the highest sequence similarity.

Non-conservative modifications of a particular polypeptide are those which substitute any amino acid not characterized as a conservative substitution. For example, any substitution which crosses the bounds of the six groups set forth above. These include substitutions of basic or acidic amino acids for neutral amino acids, (e.g., Asp, Glu, Asn, or Gln for Val, Ile, Leu or Met), aromatic amino acid for basic or acidic amino acids (e.g., Phe, Tyr or Trp for Asp, Asn, Glu or Gln) or any other substitution not replacing an amino acid with a like amino acid. Basic side chains include lysine (K), arginine (R), histidine (H); acidic side chains include aspartic acid (D), glutamic acid (E); uncharged polar side chains include glycine (G), asparagine (N), glutamine (Q), serine (S), threonine (T), tyrosine (Y), cysteine (C); nonpolar side chains include alanine (A), valine (V), leucine (L), isoleucine (I), proline (P), phenylalanine (F), methionine (M), tryptophan (W); beta-branched side chains include threonine (T), valine (V), isoleucine (I); aromatic side chains include tyrosine (Y), phenylalanine (F), tryptophan (W), histidine (H).

A polynucleotide, polypeptide, or other component is "isolated" or "purified" when it is partially or completely separated from components with which it is normally associated (other proteins, nucleic acids, cells, synthetic reagents, etc.). A polynucleotide or polypeptide is "recombinant" when it is artificial or engineered, or derived from an artificial or engineered protein or nucleic acid. For example, a polynucleotide that is inserted into a vector or any other heterologous location, e.g., in a genome of a recombinant organism, such that it is not associated with nucleotide sequences that normally flank the polynucleotide as it is found in nature is a recombinant polynucleotide. A protein expressed in vitro or in vivo from a recombinant polynucleotide is an example of a recombinant polypeptide. Likewise, a polynucleotide that does not appear in nature, for example a variant of a naturally occurring gene, is recombinant.

Any vector including a plasmid, cosmid, phage or *Agrobacterium* binary vector in double or single stranded linear or circular form which may or may not be self transmissible or mobilizable, and which can transform prokaryotic or eukaryotic host either by integration into the cellular genome or exist extrachromosomally (e.g. autonomous replicating plasmid with an origin of replication) can be used in the methods and compositions of the disclosure.

Specifically included are shuttle vectors by which is meant a DNA vehicle capable, naturally or by design, of replication in two different host organisms, which may be selected from actinomycetes and related species, bacteria and eukaryotic (e.g. higher plant, mammalian, yeast or fungal cells).

A polynucleotide in a vector is under the control of, and operably linked to, an appropriate promoter or other regulatory elements for transcription in a host cell such as a microbial, e.g. bacterial, or plant cell. The vector may be a bi-functional expression vector which functions in multiple hosts. In the case of genomic DNA, this may contain its own promoter or other regulatory elements and in the case of cDNA this may be under the control of an appropriate promoter or other regulatory elements for expression in the host cell.

The disclosure includes the terms "regulatory sequence," "control element," and "expression control sequence" to refer to polynucleotide domains comprising sequences that influence transcription initiation and rate. Regulatory sequences include, but are not limited to, promoters, promoter control elements, protein binding domains, 5' and 3' untranslated regions (UTRs), transcriptional start sites, termination sequences, polyadenylation sequences, introns, and other regulatory sequences that reside within a coding sequence.

The terms "operably linked" and "operably associated" are used interchangeably herein to broadly refer to a chemical or physical coupling (directly or indirectly) of two otherwise distinct domains in a molecule, wherein each domain has independent biological function. For example, operably linked refers to the functional connection between a regulatory sequence and the polynucleotide regulated by the regulatory sequence. For example, an operably linked swa2 polynucleotide or fragment of the disclosure can comprise a swa2 polynucleotide or fragment operably linked to a promoter, which is in turn operably linked to a polynucleotide encoding a polypeptide or inhibitory nucleic acid molecule to be expressed.

A promoter is an expression control sequence composed of a region of a DNA molecule, typically within 100 nucleotides upstream of the point at which transcription starts (generally near the initiation site for RNA polymerase II). Promoters are involved in recognition and binding of RNA polymerase and other proteins to initiate and modulate transcription. To bring a coding sequence under the control of a promoter, it typically is necessary to position the translation initiation site of the translational reading frame of the polypeptide between one and about fifty nucleotides downstream of the promoter.

A minimal promoter comprises only a necessary amount of sequence for assembly of a transcription complex required for transcription initiation. Minimal promoters typically include a "TATA box" element that may be located between about 15 and about 35 nucleotides upstream from the site of transcription initiation. Minimal promoters may also include a "CCAAT box" element (typically the sequence CCAAT) and/or a GGGCG sequence, which can be located between about 40 and about 200 nucleotides, typically about 60 to about 120 nucleotides, upstream from the transcription start site.

In plants, the constitutive plant-expressible transcription and translation regulatory element effects the expression of a downstream plant-expressible metal resistance coding sequence. Constitutive promoters include the ACT2 promoter of *Arabidopsis* (or the corresponding promoters from other plants (see, e.g., An et al. (1996) The Plant Journal 10:107-121).

"Sequence identity" herein means the extent to which two nucleotide or amino acid sequences are invariant. "Sequence alignment" means the process of lining up two or more sequences to achieve maximal levels of identity (and, in the case of amino acid sequences, conservation) for the purpose of assessing the degree of similarity. Numerous methods for aligning sequences and assessing similarity/identity are known in the art such as, for example, the Cluster Method, wherein similarity is based on the MEGALIGN algorithm, as well as BLASTN, BLASTP, and FASTA (Lipman and Pearson, 1985; Pearson and Lipman, 1988). When using all of these programs, the preferred settings are those that results in the highest sequence similarity. For example, the "identity" or "percent identity" with respect to a particular pair of aligned amino acid sequences can refer to the percent amino acid sequence identity that is obtained by ClustalW analysis (version W 1.8 available from European Bioinformatics Institute, Cambridge, UK), counting the number of identical matches in the alignment and dividing such number of identical matches by the greater of (i) the length of the aligned sequences, and (ii) 96, and using the following default ClustalW parameters to achieve slow/accurate pairwise alignments—Gap Open Penalty: 10; Gap Extension Penalty: 0.10; Protein weight matrix: Gonnet series; DNA weight matrix: IUB; Toggle Slow/Fast pairwise alignments=SLOW or FULL Alignment.

Two sequences are "optimally aligned" when they are aligned for similarity scoring using a defined amino acid substitution matrix (e.g., BLOSUM62), gap existence penalty and gap extension penalty so as to arrive at the highest score possible for that pair of sequences. Amino acid substitution matrices and their use in quantifying the similarity between two sequences are well-known in the art and described, e.g., in Dayhoff et al. (1978) "A model of evolutionary change in proteins" in "Atlas of Protein Sequence and Structure," Vol. 5, Suppl. 3 (ed. M. O. Dayhoff), pp. 345-352. Natl. Biomed. Res. Found., Washington, D.C. and Henikoff et al. (1992) Proc. Nat'l. Acad. Sci. USA 89: 10915-10919. The BLOSUM62 matrix (FIG. 10) is often used as a default scoring substitution matrix in sequence alignment protocols such as Gapped BLAST 2.0. The gap existence penalty is imposed for the introduction of a single amino acid gap in one of the aligned sequences, and the gap extension penalty is imposed for each additional empty amino acid position inserted into an already opened gap. The alignment is defined by the amino acids positions of each sequence at which the alignment begins and ends, and optionally by the insertion of a gap or multiple gaps in one or both sequences so as to arrive at the highest possible score. While optimal alignment and scoring can be accomplished manually, the process is facilitated by the use of a computer-implemented alignment algorithm, e.g., gapped BLAST 2.0, described in Altschul et al. (1997) Nucl. Acids Res. 25: 3389-3402, and made available to the public at the National Center for Biotechnology Information (NCBI) Website (www.ncbi.nlm.nih.gov). Optimal alignments, including multiple alignments, can be prepared using, e.g., PSI-BLAST, available through the NCB1 website and described by Altschul et al. (1997) Nucl. Acids Res. 25:3389-3402.

With respect to an amino acid sequence that is optimally aligned with a reference sequence, an amino acid residue "corresponds to" the position in the reference sequence with which the residue is paired in the alignment. The "position" is denoted by a number that sequentially identifies each amino acid in the reference sequence based on its position relative to the N-terminus. Owing to deletions, insertion, truncations, fusions, etc., that must be taken into account when determining an optimal alignment, in general the amino acid residue number in a test sequence as determined by simply counting from the N-terminal will not necessarily be the same as the number of its corresponding position in the reference sequence. For example, in a case where there is a deletion in an aligned test sequence, there will be no amino acid that corresponds to a position in the reference sequence at the site of deletion. Where there is an insertion in an aligned reference sequence, that insertion will not correspond to any amino acid position in the reference sequence. In the case of truncations or fusions there can be stretches of amino acids in either the reference or aligned sequence that do not correspond to any amino acid in the corresponding sequence.

The term "transformation" means the introduction of a foreign (i.e., extrinsic or extracellular) gene, DNA or RNA sequence to a host cell, so that the host cell will express the introduced gene or sequence to produce a desired substance, typically a protein or enzyme coded by the introduced gene or sequence. The introduced gene or sequence may include regulatory or control sequences, such as start, stop, promoter, signal, secretion, or other sequences used by the genetic machinery of the cell. A host cell that receives and expresses introduced DNA or RNA has been "transformed" and is a "transformant" or a "clone." The DNA or RNA introduced to a host cell can come from any source, including cells of the same genus or species as the host cell, or cells of a different genus or species.

As will be understood by those of skill in the art, it can be advantageous to modify a coding sequence to enhance its expression in a particular host. The genetic code is redundant with 64 possible codons, but most organisms preferentially use a subset of these codons. The codons that are utilized most often in a species are called optimal codons, and those not utilized very often are classified as rare or low-usage codons (see, e.g., Zhang et al. (1991) Gene 105:61-72). Codons can be substituted to reflect the preferred codon usage of the host, a process sometimes called "codon optimization" or "controlling for species codon bias."

Optimized coding sequences containing codons preferred by a particular prokaryotic or eukaryotic host (see also, Murray et al. (1989) Nucl. Acids Res. 17:477-508) can be prepared, for example, to increase the rate of translation or to produce recombinant RNA transcripts having desirable properties, such as a longer half-life, as compared with transcripts produced from a non-optimized sequence. Translation stop codons can also be modified to reflect host preference. For example, preferred stop codons for *S. cerevisiae* and mammals are UAA and UGA, respectively. The preferred stop codon for monocotyledonous plants is UGA, whereas insects and *E. coli* prefer to use UAA as the stop codon (Dalphin et al. (1996) Nucl. Acids Res. 24: 216-218). Methodology for optimizing a nucleotide sequence for expression in a plant is provided, for example, in U.S. Pat. No. 6,015,891, and the references cited therein.

Various regulatory sequences can be operably linked to a coding sequence to facilitate expression in a desired host cell. Such regulatory sequences include promoters or enhancers as well as other sequences that facilitate polymerase binding and termination. In the present context, a promoter is a DNA region which includes sequences sufficient to cause transcription of an associated (downstream) sequence. The promoter may be regulated, i.e., not constitutively acting to cause transcription of the associated sequence. If inducible, there are sequences present which mediate regulation of expression so that the associated sequence is transcribed only when an inducer is available to the plant or plant tissue.

A coding sequence or a polynucleotide is downstream of second nucleic acid portion or sequence when it is located 3' of the second sequence. A coding sequence or a polynucleotide is upstream of a second DNA portion or sequence when it is located 5' of that sequence.

A polynucleotide is said to encode a polypeptide if, in its native state or when manipulated by methods known to those skilled in the art, it can be transcribed and/or translated to produce the polypeptide or a fragment thereof. The anti-sense strand of such a polynucleotide is also said to encode the sequence.

A nucleotide sequence is operably linked when it is placed into a functional relationship with another nucleotide sequence. For instance, a promoter is operably linked to a coding sequence if the promoter effects its transcription or expression. Generally, operably linked means that the sequences being linked are contiguous and, where necessary to join two protein coding regions, contiguous and in reading frame. However, it is well known that certain genetic elements, such as enhancers, may be operably linked even at a distance, i.e., even if not contiguous.

The term recombinant polynucleotide refers to a polynucleotide which is made by the combination of two otherwise separated segments of sequence accomplished by the artificial manipulation of isolated segments of polynucleotides by genetic engineering techniques or by chemical synthesis. In so doing one may join together polynucleotide segments of desired functions to generate a desired combination of functions.

Polynucleotide probes include an isolated polynucleotide attached to a label or reporter molecule and may be used to identify and isolate other SWA2 homologs or orthologs or in determining the expression of a particular SWA2 mutant or variant. Probes comprising synthetic oligonucleotides or other polynucleotides may be derived from naturally occurring or recombinant single or double stranded nucleic acids or be chemically synthesized. Polynucleotide probes may be labeled by any of the methods known in the art, e.g., random hexamer labeling, nick translation, or the Klenow fill-in reaction.

The transgenic plants comprising a modified polyamine production capacity can then be used in the environments comprising metal/aluminum contamination. Such transgenic plants can be used for phytorediation of the contaminated environment.

The term "phytoremediation" is used herein as it will be well understood by those skilled in the art to include any of (i) phytoextraction, when metal-accumulating plants are employed to extract metals from contaminated soil; (ii) phytostabilization, when metal-tolerant plants, (known as "excluders"), are used to reduce or exclude the environmental risk in heavy metals; (iii) phytodegradation, when plants are applied to degrade nonvolatile hydrocarbons, thus removing them from the environment. As shown in the examples, the disclosure provides compositions and methods for phytoremediation contaminated soil.

The "environment" may be any site which it is desired to phytoremediate e.g. which is contaminated with organic or metal pollutants. Examples include sites contaminated with oil near drilling rigs, oil refineries, near mines, power stations, metalurgical plants and so forth.

A "metal" to which the compositions and methods may be used include any one or more of lead, copper, cadmium, nickel, mercury, arsenic, selenium strontium, aluminum or zinc.

Soils containing excessive aluminum or heavy metals may be unable to grow plants in a manner suitable for agriculture. The disclosure includes a method conferring to a plant the ability to grow in aluminum or heavy metal containing soil. The plant may be grown in a growth medium such as a solid medium, semi-solid medium, liquid medium or a combination thereof. It may include soil, sand, sludge, compost, or artificial soil mix. The shoot (leaf or stem) or and root biomass may be harvested. Typically, a sufficient portion of the shoot biomass is not harvested and is left in the growth media to permit continued plant growth.

As will be recognized in areas of agriculture or places where agriculture is desired, high levels of aluminum in the soil or growth medium of a plant result in toxicity to the roots and plant resulting in cell death. Transgenic plants capable of growing on such medium would increase the agricultural land, currently unavailable due to aluminum levels. Accordingly, various crop plants can be modified using the methods, polynucleotides, polypeptides and compositions herein to provide plants capable of growing in/on toxic soils.

The disclosure also provides a method of identifying agents that can promote plant growth on aluminum toxic environments, comprising culturing a plant having (i) an als7-1 genotype, (ii) a mutation in SLOW WALKER2 that reduces S-adenosylmethionine recycling, or (iii) a reduction in S-adenosylmethionine recycling, culturing the plant in an aluminum containing environment and contacting the plant with an agent suspected of inhibiting Al toxicity, wherein if the agent improves plant growth compared to a plant not contacted with the agent, the agent inhibits aluminum toxicity. The disclosure provides variant polynucleotides that confer aluminum sensitivity in a plant organism. Based on genomic location and analysis, als7-1 was identified as having a defect in an Al-exclusion mechanism. Cloning of the als7-1 mutation showed that it negatively affects the gene encoding the putative nucleolar localized ribosomal biogenesis factor SLOW WALKER2 (At1g72440), which is required for normal gametogenesis and mitotic progression. Molecular analysis revealed that Al hypersensitivity in als7-1 is correlated with loss of expression of a factor required for S-adenosylmethionine recycling, which leads to reduced levels of endogenous polyamines. Such modified functions in plants are useful in screening assays to identified agents the reduce aluminum uptake thus in the presence of an agent that inhibits uptake providing the ability to grown in/on aluminum toxic soils or soils having high levels of aluminum.

As used herein with respect to any of the embodiments above, the term "metal resistance" means that (1) a plant or soil has been treated to allow plant growth or improved plant growth using a polyamine composition; or (b) a non-naturally occurring plant is not inhibited by the presence of at least one ionic form of a metal at concentrations (levels) at which a naturally occurring (wild-type) counterpart of the non-naturally occurring organism is inhibited or exhibits symptoms of toxicity. It is not intended that the term metal resistance refer to resistance to unlimited concentrations of metal ions, but rather the term is relative in that it relies on comparison to the properties of a parental strain. Resistance is measured relative to the sensitivity of a comparison wild-type plant to the toxic metal, and resistance is not to unlimited levels.

For example, "aluminum resistance" means that a plant treated with a polyamine is more tolerate to growth in an aluminum contaminated soil or water or a non-naturally occurring transgenic plant is capable of growing more effectively than a wild-type plant on the aluminum contaminated environment. Resistance is measured relative to the sensitivity of a comparison plant not contacted with a polyamine in a similar metal contaminated soil or water.

Metal (e.g., aluminum and cadmimum) resistant plants are useful for revegetation of contaminated soils (e.g., toxic metals subsequent to mining operations) and/or bioremediation of soils and/or aquatic environments contaminated with aluminum metals.

The following examples are meant to illustrate but not limit the disclosure. Other modifications and changes in techniques and material sources will be apparent to those of skill in the art.

Examples

Plant Growth Conditions

For all growth experiments performed, Col-0 wt and mutant seeds were surface-sterilized with household bleach and cold stratified for 4 d at 4° C. in the dark for synchronization of germination. Seeds were subsequently suspended in 0.15% (w/v) agarose and for planting on either soaked gel plates or hydroponic plates. Further description of the growth experiments can be found in Larsen, P. B., Geisler, M. J. B., Jones, C. A., Williams, K. M., and Cancel, J. D. (2005), ALS3 encodes a phloem-localized ABC transporter-like protein that is required for aluminum tolerance in Arabidopsis. Plant J. 41, 353-63. All growth analyses were done in a Percival 136LLVL plant growth chamber under a 24 hr light cycle at 20° C. Adult plants were grown in soil under a 24 hr light cycle at 20° C. in a plant growth room supplemented with Sylvania Gro-Lite® fluorescent bulbs.

ICP-OES Analysis.

In order to determine total Al content, roots of 5 d old Col-0 wt and als7-1/swa2-2 grown hydroponically were exposed to either 0 or 25 μM $AlCl_3$ (pH 4.2) for 48 h, after which the terminal 25% (approximately 3-4 mm) of washed sample roots was harvested, dried, and asked in pure nitric acid. Samples were resuspended in 5 mls of 1% nitric acid and analyzed using a Perkin-Elmer Optima 7300 DV ICP-OES.

Determination of Polyamine Content.

For measurement of polyamine content, root tissue was harvested and ground in 10 mM Tris-HCl, pH 7.5 after which samples centrifuged for 5 minutes at 4° C. Supernatants were collected and digested with ice-cold 0.2N perchloric acid (PCA) at a concentration of 100 mg of tissue per 1 mL PCA for 15 minutes on ice. Samples were centrifuged for 10 minutes at 4° C. after which the supernatants were analyzed for polyamines using HLPC with an Agilent 1100 with autosampler, a Hitachi F1000 fluorescence detector, with the Agilent's ChemStation software (Gilbert, R. S., Gonzalez, G. G., Hawel, L. 3rd, & Byus, C. V. (1991) An ion-exchange chromatography procedure for the isolation and concentration of basic amino acids and polyamines from complex biological samples prior to high-performance liquid chromatography. Anal. Biochem. 199, 86-92). Protein concentrations were quantified using the microassay procedure of the Bio-Rad Protein Assay (Bio-Rad, Hercules, Calif.).

Map-Based Cloning.

A mapping population was generated from a cross of als7-1/swa2-2 (male; ecotype Col-0) to Ws-0 wt (female) after which seven-day-old F2 seedlings that displayed the als7-1/swa2-2 phenotype when grown on nutrient medium soaked with 0.75 mM $AlCl_3$ (pH 4.2) were isolated and planted in soil for isolation of genomic DNA from adult leaves. Genomic DNA was prepared as described (Larsen, supra.) and used as a template for PCR-based mapping.

For generation of a narrow genetic window, a novel CAPS marker, At1g72480, was identified. Primers for this marker were 5'-ATGCAGAAGCGAATAGCCTTG-3' (SEQ ID NO:1) and 5'-CAAAATCCAGATAAGCACCTC-3' (SEQ ID NO:2), with AccI digestion giving two DNA fragments for Col-0 and one for Ws. Candidate genes were identified following generation of a narrow genetic window based on the published *Arabidopsis* genomic sequence. Candidates were amplified by high fidelity PCR using primers designed to the predicted 5' and 3' untranslated regions of each gene with Pfu Turbo Taq polymerase (Stratagene). PCR products were subcloned into pGemT-easy (Promega) for sequencing. Generated sequences were compared to the published *Arabidopsis* genomic sequence to identify potential mutations.

Functional Complementation Analysis and Allele Identification.

Functional complementation analysis was done by subcloning a PCR generated genomic construct representing 1 kB of upstream promoter sequence, 5'UTR, all exons and introns, and 3' UTR for At1g72440 into pBI101. This construct was introduced into the als7-1/swa2-2 mutant by *Agrobacterium*-mediated transformation and primary transformants were selected by screening for kanamycin resistance. T2 plants were subsequently analyzed by growth for 7 d on nutrient agar plates soaked with 0.75 mM $AlCl_3$ (pH 4.2).

Work related to TILLING for the als7-2/swa2-3 allele was performed by the Seattle TILLING project at the Fred Hutchinson Cancer Research Center at the University of Washington.

Northern and qPCR Analysis.

For determination of organ specific patterns of SWA2 expression, roots that were either untreated or treated with 25 μM $AlCl_3$ (pH 4.2) were collected from 7 d old hydroponically grown *Arabidopsis* seedlings. Untreated leaves, stems, and flowers were collected from 4 wk old adult plants. Tissue was harvested and immediately frozen for RNA extraction and Northern analysis as previously described (Larsen et al., 2005). qPCR analysis was performed as previously described (Rounds and Larsen, 2008). For analysis of AtARD3 expression, the primers used were 5'-AAGATACAAATTCCTTAGGATCC-3' (SEQ ID NO:3) and 5'-ACACAAAAGAAGAATAACCATGG-3' (SEQ ID NO:4). For analysis of At4g10500 expression, the primers used were 5'-TTCCGACTTTCTATTTCCCTTC-3' (SEQ ID NO:5) and 5'-ATAGCTTAAAGAGCCAATTCAAG-3' (SEQ ID NO:6). ACT2 primers were as previously described (Rounds, M. A., & Larsen, P. B. (2008) Aluminum dependent root growth inhibition results from AtATR dependent cell cycle arrest and loss of the quiescent center in *Arabidopsis*. Curr. Biol. 18, 1495-1500).

Subcellular Localization of ALS7.

Transgenic plants for $PRO_{SWA2}$:SWA2:GFP analysis were generated by subcloning a genomic construct representing 1 kB of upstream sequence, 5' UTR, all exons and all introns for SWA2 without the native stop codon as a translational fusion to the full coding sequence for GFP into pBI101. This construct was transformed into Col-0 wt by *Agrobacterium*-mediated transformation and primary transformants were selected by screening for kanamycin resistant seedlings. For analysis of subcellular localization, homozygous T2 lines were analyzed using a Leica SP2 confocal laser microscope, using a FITC filter for excitation. For localization of nuclei, seedlings were stained with 15 μg/ml DAPI for 30 minutes prior to visualization.

Al Hypersensivity of als7-1 Results from Increased Al Uptake.

A previously characterized *Arabidopsis* mutant with increased sensitivity to Al, als7-1, was studied further to determine the nature of its increase in Al dependent root growth inhibition (Larsen et al., 1996). A dose response analysis using a previously described Al-soaked gel system was performed in order to compare the growth of Col-0 wt and als7-1 in the presence of a range of Al concentrations (pH 4.2). While als7-1 roots have a mild growth defect compared to Col-0 wt even in the absence of Al, exposure to as little as 0.25 mM $AlCl_3$ in this Al-soaked gel system resulted in significantly greater root growth inhibition for als7-1 roots compared to roots of Col-0 wt (FIGS. 1A and C). Treatment with increasing concentrations of Al resulted in an increase in the differential in root growth inhibition for als7-1 compared to Col-0 wt, with als7-1 roots being extremely sensitive to concentrations of $AlCl_3$ that had only modest effects on Col-0 wt root growth. Similar results were seen for als7-1 when it was grown in a hydroponic environment supplemented with increasing concentrations of $AlCl_3$ (pH 4.2) (FIG. 1B). Even though als7-1 root growth is significantly compromised in the absence of Al, addition of 25 μM $AlCl_3$ resulted in severe root growth inhibition for als7-1 roots compared to Col-0 wt, which is consistent with the observed Al hypersensitivity seen in the Al-soaked gel system.

Prior work on the als7-1 mutant suggested that its roots had reduced levels of Al-induced callose and Al accumulation compared to Col-0 wt, which represented a paradox when considering the increase in Al sensitivity seen for this mutant (Larsen et al., 1996). In contrast to this prior work, the disclosure shows that als7-1 roots are fully capable of producing callose following Al treatment, thus suggesting that the previous report regarding this strictly qualitative measure was incorrect (FIG. 1D). Additionally, determination of total Al content using ICP-OES revealed that, unlike the previous report that used a qualitative method for estimating Al content (Larsen et al., 1996), als7-1 roots accumulate significantly more Al than Col-0 wt following Al exposure (FIG. 1E). Finally, Northern analysis of Al-treated Col-0 wt and als7-1 roots revealed that als7-1 roots have significantly greater Al-inducible expression of AtALMT1 (FIG. 1F), which encodes a malate transporter required for Al resistance (Hoekenga et al., 2006). Taken together, these results indicate that the increase in Al sensitivity seen for als7-1 roots arises from reduced capability to exclude Al, thus demonstrating that ALS7 is required for a mechanism of Al resistance.

Als7-1 is a Partial Loss-of-Function Mutation in *Arabidopsis* SLOW WALKER2.

In order to determine the nature of the als7-1 mutation, a map based cloning approach was undertaken, with the als7-1 mutation being localized to the bottom arm of chromosome 1. Sequence analysis of gene candidates within the narrowly defined window revealed a nucleotide substitution at the splice site between the fifth exon and subsequent intron of the previously described gene, SLOW WALKER2 (Li et al., 2009), which is required for normal development and mitotic progression of the female gametophyte in a currently unknown manner (FIGS. 2A and B). While an unusual substitution for an EMS-mutagenized population, no other mutations were found in this genetic window after exhaustive sequence analysis. It is likely that this nucleotide substitution leads to improper mRNA processing for At1g72440, thus causing reduced SWA2 function.

Sequence analysis of SWA2 utilizing Interpro Scan (Zdobnov and Apweiler, 2001) indicates that SWA2 has a "CCAAT-Box Binding Factor" (CBF) domain which functions to stimulate transcription from the HSP70 promoter (Lum et al., 1990). Utilizing BLAST, it was found that it has similarity to the enhancer binding protein zeta from rat, human and mouse with each having 33% identity and 51% similarity to *Arabidopsis* SWA2. The human CBF (hCBF) has been described to work in conjunction with proteins such as p53 to control transcription of a growth regulated hsp70 gene in HeLa cells (Lum et al., 1990). Since SLOW WALKER2 has been proposed to be involved in ribosome biogenesis (Li et al., 2009), yet homologs such as hCBF are directly involved in transcription, it is currently unclear as to what role SWA2 plays in the nucleolus.

In order to confirm the verity of the identified mutation, a functional complementation approach was utilized in which the wild type version of At1g72440, including 1 Kb of the promoter region, the 5'-UTR, all exons and introns, and the 3'-UTR, was introduced by *Agrobacterium*-mediated transformation into als7-1/swa2-2. Following this, root growth of identified transgenic lines in the presence of Al was determined and compared to Col-0 wt and als7-1/swa2-2. As shown in FIG. 2B, functional complementation of als7-1/swa2-2 resulted in full restoration of root growth in the presence of a level of AlCl3 that is highly inhibitory to roots of als7-1/swa2-2.

Since the previously described swa2-1 loss-of-function allele has been reported as being embryo lethal, a TILLING approach was utilized to identify additional non-lethal loss-of-function alleles of swa2 to confirm that the increased Al sensitivity seen for als7-1/swa2-2 arises from the identified mutation. Using the TILLING approach, an allele that represented an EMS-induced nucleotide change in exon 14 of At1g72440 (als7-2/swa2-3) was identified (FIGS. 2A and B) and tested for its capability to grow in the presence of Al. This mutation represents an amino acid substitution in the predicted "CCAAT binding domain" of SWA2. Roots of als7-1/swa2-2 and als7-2/swa2-3 were indistinguishable when grown on moderate levels of Al that had only a modest inhibitory effect on Col-0 wt root growth (FIG. 2C).

It was also of interest to determine the expression pattern of At1g72440, especially with regard to Al inducibility. For this analysis, Col-0 wt and als7-1 seedlings were grown hydroponically in the absence or presence of 25 µM AlCl$_3$ (pH 4.2), after which root tissue was collected for isolation of total RNA. Northern analysis revealed detectable levels of SWA2 in Col-0 wt root tissue, yet no increase in SWA2 expression was seen following Al treatment (FIG. 2E). Surprisingly, als7-1 roots showed a constitutive increase in expression of SWA2 compared to Col-0 wt, suggesting that the als7-1 allele may affect transcript turnover in an unknown manner. Further analysis showed that along with being expressed in roots, SWA2 is weakly expressed in leaves and stems along with a higher level of expression in flowers, which is consistent with its role in gametophyte development (FIG. 2E).

SWA2 is Localized to the Nucleolus in Cells of the Root Tip.

For a factor to participate in a mechanism of Al resistance, it is expected that such a factor would at the minimum be localized to the root tip since this is the site at which Al toxicity occurs. In order to determine this, a tissue localization approach using a SWA2:GFP translational fusion that was under the control of the SWA2 promoter was utilized. Transgenic lines expressing the PROSWA2:SWA2:GFP construct were subsequently grown in the absence or presence of 25 µM AlCl$_3$ (pH 4.2), after which confocal microscopy was used to determine the tissue and subcellular compartment to which SWA2 is localized. Fluorescence from SWA2:GFP was observed predominantly in cells of the root tip strictly in the nucleoli (FIGS. 3A and B). There was no change in pattern of localization when comparing untreated to Al treated roots (FIGS. 3B and C). Examination of more mature regions of the root revealed that SWA2:GFP fluorescence was coincident with regions where lateral roots emerged (FIG. 3E-H), indicating that SWA2 participates in lateral root development.

SWA2 is Required for Normal Gene Expression Following Al Treatment.

The strict nucleolar localization pattern of SWA2 and its similarity to hCBF, suggests that it functions in some capacity that is related to gene expression. Because of this, preliminary microarray analysis was performed to identify gene candidates that may have altered expression due to loss of SWA2 function. From this preliminary analysis, it was determined that expression of two genes in particular was severely decreased in roots of Al-treated als7-1/swa2-2 compared to Col-0 wt. Expression of both AtARD3 (At2g26400), which is an acireductone dioxygenase, and At4g10500, which is a member of the 2-oxoglutarate and Fe (II)-dependent oxygenase superfamily, was severely reduced in als7-1/swa2-2 roots following Al exposure (FIG. 4A-B).

Acireductone dioxygenases are required for S-adenosyl-methionine (SAM) recycling, which occurs in a methionine dependent manner. Loss of SAM recycling would be predicted to result in reduced production of SAM byproducts such as the polyamines spermidine and spermine. Since AtARD3 represents a step in SAM recycling prior to production of methionine, it was tested what effect addition of exogenous L-methionine would have on root growth of als7-1/swa2-2 roots in the presence of Al. Supplementation of the Al-soaked gel growth medium with 10 µM L-methionine resulted in a measurable increase in growth of als7-1/swa2-2 roots in the presence of a level of AlCl$_3$ that is highly inhibitory to the mutant, thus suggesting that SAM deficiency may contribute to the Al hypersensitivity phenotype of als7-1/swa2-2 roots (FIG. 4C).

als7-1 Al Hypersensitivity is Correlated with Reduced Polyamine Content.

Polyamines represent a class of small aliphatic polycatonic molecules that are found in almost all organisms that have a myriad of functions including maintenance of DNA structure, promotion of RNA processing, stabilization of membranes, and scavenging reactive oxygen species. Spermine is a common polyamine that is synthesized in a manner directly dependent on available pools of SAM. Because als7-1/swa2-2 likely has a defect in SAM recycling in the presence of Al, it was determined whether als7-1/swa2-2 roots had reduced endogenous polyamine levels. For this analysis, HPLC was used to determine the spermine content in roots of both Col-0 wt and als7-1/swa2-2. As shown in FIG. 5A, the level of spermine was significantly reduced in roots of als7-1/swa2-2, demonstrating that a consequence of the als7-1/swa2-2 mutation is impaired capability to produce spermine likely due to reduced capability for SAM recycling.

Since spermine content was reduced in als7-1/swa2-2, it was subsequently determined whether addition of exogenous spermine would have a promotive effect on root growth in the presence of normally toxic levels of AlCl$_3$. As shown in FIG. 5B, addition of as little as 25 µM spermine to roots grown in the presence of 25 or 50 µM AlCl$_3$ in a hydroponic environment (pH 4.2) resulted in upwards of a 6-fold increase in root growth for both Col-0 wt and als7-1/swa2-2. In contrast, addition of 1.5 mM difluoromethyl-ornithine (DFMO), which is an inhibitor of the enzyme ornithine decarboxylase that catalyzes the conversion of ornithine to putrescine (19), to the hydroponic growth medium resulted in a measurable decrease in Al resistance of Col-0 wt roots (FIG. 5C). Interestingly, addition of spermine in the presence of either 25 or 50 µM AlCl$_3$ resulted in almost full restoration of als7-1/swa2-2 root growth, whereas Col-0 wt roots remained significantly inhibited compared to untreated controls. Consequently, addition of spermine had a greater effect on als7-1/swa2-2 root growth in the presence of Al compared to Col-0 wt, which is consistent with the Al hypersensitivity of the mutant resulting from reduced endogenous levels of spermine.

Because polyamines promote root growth in the presence of Al, it was of interest to determine whether they are required for a mechanism of Al tolerance or resistance. Al accumulation was measured for roots that were grown either in the absence or presence of 25 µM spermine in order to differentiate between these two mechanisms since increased tolerance represents improved capability to cope with internalized Al whereas increased resistance arises from enhanced capability to exclude Al. From this analysis it was found that treatment of Col-0 wt roots with spermine resulted in a significant reduction in Al uptake compared to the Al-treated control (FIG. 5D). In conjunction with the finding that als7-1/swa2-2 roots have an increase in Al accumulation that is correlated with reduced spermine content (FIG. 1E), it is thus demonstrated that endogenous polyamines are useful to limit the amount of Al that is internalized presumably by competing for binding to extra- and intracellular anionic sites.

The foregoing examples are meant to be illustrative but not limiting and should not be construed as the only methods, compositions or agents that can be used in the practice of the invention. The foregoing examples are not meant to limit the following claims.

What is claimed is:

1. A method for phytoremediation of soil, groundwater, industrial waste or water, wherein the soil, groundwater, industrial waste or water is contaminated with at least one metal ion selected from the group consisting of aluminum, copper, cobalt, zinc, antimony, mercury, cadmium, arsenate and arsenite, the method comprising the step of contacting an *Arabidopsis thaliana* plant comprising an als7-1 genotype mutation with at least one polyamine agent that promotes polyamine synthesis or polyamine levels in the plant, wherein the als7-1 genotype mutation comprises a nucleotide substitution at a splice junction between the $5^{th}$ exon and subsequent intron of SWA2/At1g72440 such that the splice junction comprises the sequence: 5'-GAACAAGttattg-3' (SEQ ID NO:15), wherein the *Arabidopsis thaliana* plant takes up the at least one metal ion from the soil, groundwater, industrial waste or water when the *Arabidopsis thaliana* plant is grown in the contaminated soil, groundwater, industrial waste or water and is contacted with the at least one polyamine agent.

2. The method of claim 1, wherein the metal ion is an aluminium ion.

3. The method of claim 1, wherein the at least one polyamine agent that increases polyamine levels is selected from the group consisting of putrescine, spermidine, spermine, cadaverine or a composition including at least one of these compounds.

4. The method of claim 1, wherein the at least one polyamine agent is spermine.

5. The method of claim 1, wherein the at least one polyamine agent is at least one compound selected from the group consisting of 1,3-diaminopropane, putrescine, cadaverine, cardine, spermidine, homospermidine, aminopropylcadaverine, termine, spermine, thermospermine, canavalmine, aminopentylnorspermidine, N,N-bis(aminopropyl)cadaverine, homospermine, caldopentamine, homocaldopentamine, caldohexamine, and homocaldohexamine.

6. The method of claim 5, wherein the at least one polyamine agent comprises two or more polyamine agents.

* * * * *